United States Patent
Suzuki et al.

(10) Patent No.: US 7,956,141 B2
(45) Date of Patent: Jun. 7, 2011

(54) METAL COMPLEX CONTAINING TRIDENTATE LIGAND, AND POLYMERIZATION CATALYST COMPRISING THE SAME

(75) Inventors: Toshiaki Suzuki, Wako (JP); Lixin Zhang, Wako (JP); Zhaomin Hou, Wako (JP)

(73) Assignee: Riken, Saitama (JP)

( * ) Notice: Subject to any disclaimer, the term of this patent is extended or adjusted under 35 U.S.C. 154(b) by 758 days.

(21) Appl. No.: 11/795,571

(22) PCT Filed: Jan. 23, 2006

(86) PCT No.: PCT/JP2006/000978
§ 371 (c)(1),
(2), (4) Date: Jul. 19, 2007

(87) PCT Pub. No.: WO2006/078021
PCT Pub. Date: Jul. 27, 2006

(65) Prior Publication Data
US 2008/0114136 A1   May 15, 2008

(30) Foreign Application Priority Data

Jan. 21, 2005  (JP) ................ 2005-014217

(51) Int. Cl.
*B01J 31/22* (2006.01)
*C08F 4/52* (2006.01)
*C08F 36/04* (2006.01)
*C08F 36/06* (2006.01)
*C08F 36/08* (2006.01)

(52) U.S. Cl. ..... 526/172; 526/134; 526/335; 526/340.2; 526/340.4; 526/346; 526/347; 502/162; 502/167; 556/9; 556/13

(58) Field of Classification Search ............... 556/9, 13, 556/44; 502/162, 167; 526/134, 172, 335, 526/340.2, 240.4, 346, 347
See application file for complete search history.

(56) References Cited

U.S. PATENT DOCUMENTS
2005/0137382 A1   6/2005 Liang
2005/0288504 A1*  12/2005 Liang ................ 546/2

FOREIGN PATENT DOCUMENTS
JP   2001-520696 A   10/2001
JP   2002-513823 A    5/2002
JP   2004-513998 A    5/2004
WO   WO-9846651 A2   10/1998

OTHER PUBLICATIONS

Arnold, Polly L. et al., Symmetric and asymmetric samarium alkoxide derivatives of bridging sulfur biphenolate and binaphtholate ligands; synthetic, structural, and catalytic studies, Journal of Organometallic Chemistry, 2002, vol. 647, pp. 205-215.
Fan, Lei et al., N-C Cleavage in Pincer PNP Complexes of Palladium, Organometallics, 2004, vol. 23, pp. 4778-4787.
Fryzuk, Michael D. et al., Synthesis and Characterization of the Five-Coordinate Scandium Dialkyl Complexes $ScR_2[N(SiMe_2CH_2PPr^i_2)_2]$ (R= Me, Et, $CH_2SiMe_3$), Organometallics, 1996, vol. 15, pp. 3329-3336.
Fryzuk, Michael D. et al., Synthesis, characterization, and reactivity of scandium chloro, alkyl, aryl, and borohydride complexes, Sc ($\eta^5$-$C_5H_5$)R[N(SiMe$_2$CH$_2$P$^i$Pr$_2$)$_2$] (R= Cl, Me, Ph, and BH$_4$), Can. J. Chem., 2000, vol. 78, pp. 1003-1012.
Huang, Mei-Hui at al., Amido Pincer Complexes of Palladium: Synthesis, Structure, and Catalytic Heck Reaction, Organometallics, 2004, vol. 23, pp. 2813-2816.
Kaita, Shojiro et al., An Efficient Gadolinium Metallocene-Based Catalyst for the Synthesis of Isoprene Rubber with Perfect 1,4-Cis Microstructure and Marked Reactivity Difference between Lanthanide Metallocenes toward Dienes As Probed by Butadiene—Isoprene Copolymerization Catalysis, Macromolecules, 2004, vol. 37, pp. 5860-5862.

* cited by examiner

*Primary Examiner* — Caixia Lu
(74) *Attorney, Agent, or Firm* — Birch, Stewart, Kolasch & Birch, LLP

(57) ABSTRACT

The present invention provides 1) a complex comprising a mono-anionictridentate ligand, represented by the following general formula (I); 2) a polymerization catalyst composition, comprising the complex; and 3) a cis-1,4-isoprene polymer, a cis-1,4-butadiene polymer, a cis-1,4-isoprene-styrene copolymer, a cis-1,4-butadiene-styrene copolymer, a cis-1,4-butadiene-cis-1,4-isoprene copolymer, and a cis-1,4-butadiene-cis-1,4-isoprene-styrene copolymer, each of which has high-cis-1,4 content in a micro structure and a sharp molecular-weight distribution.

(I)

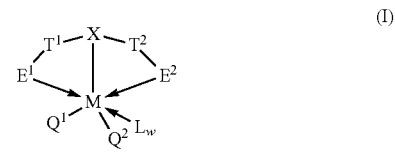

16 Claims, 17 Drawing Sheets

[Figure 1]
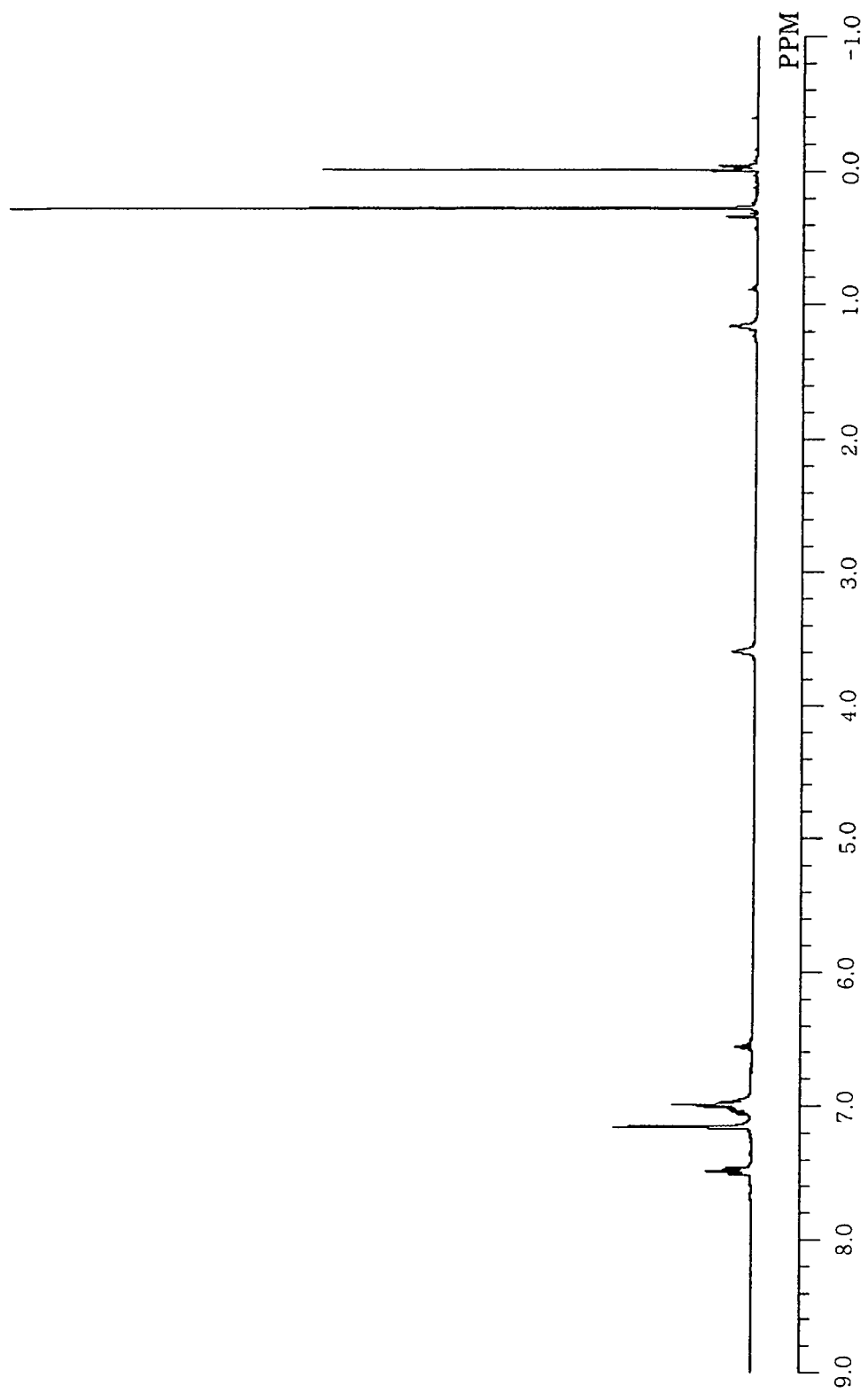

[Figure 2]
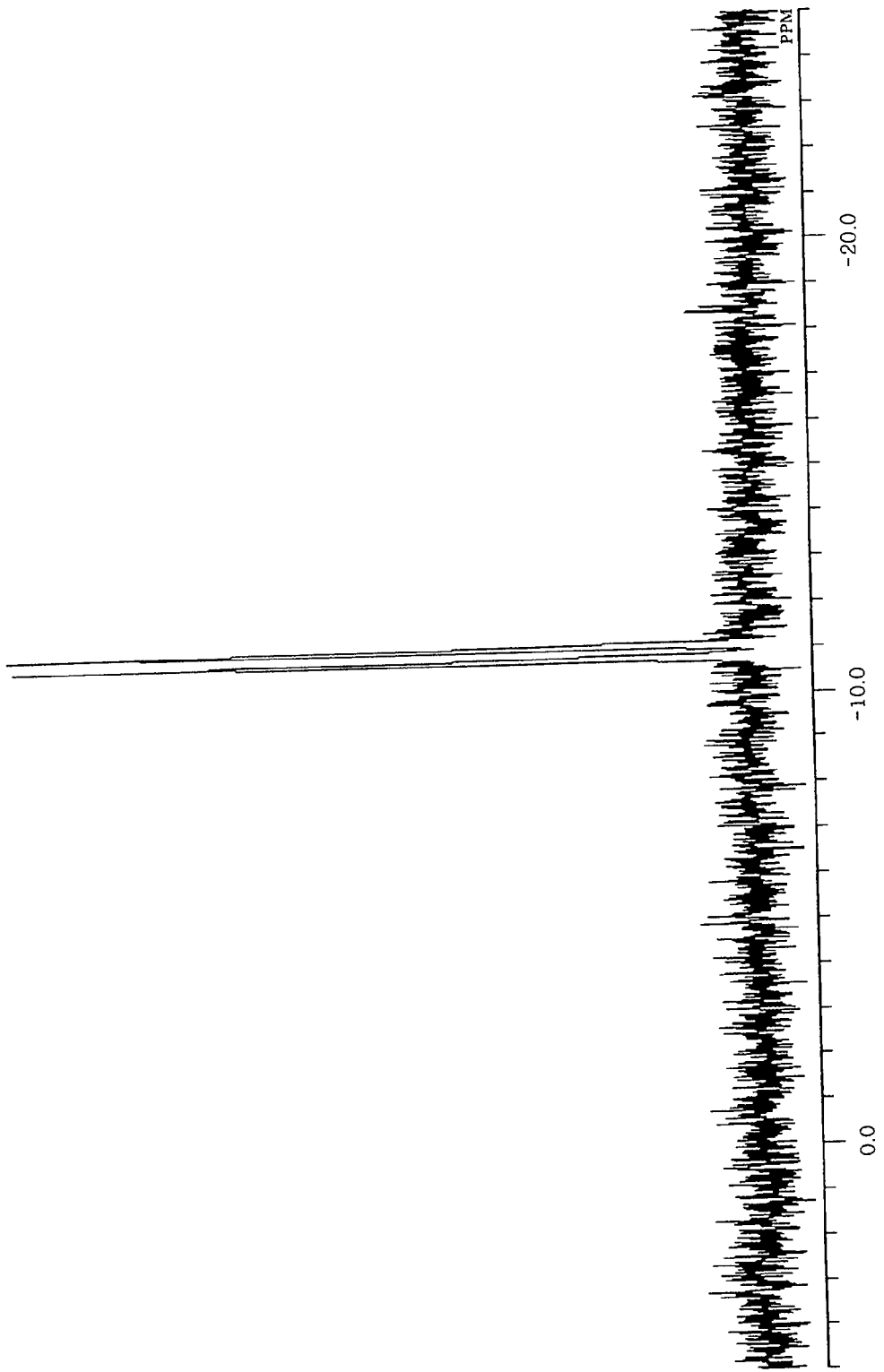

[Figure 3]
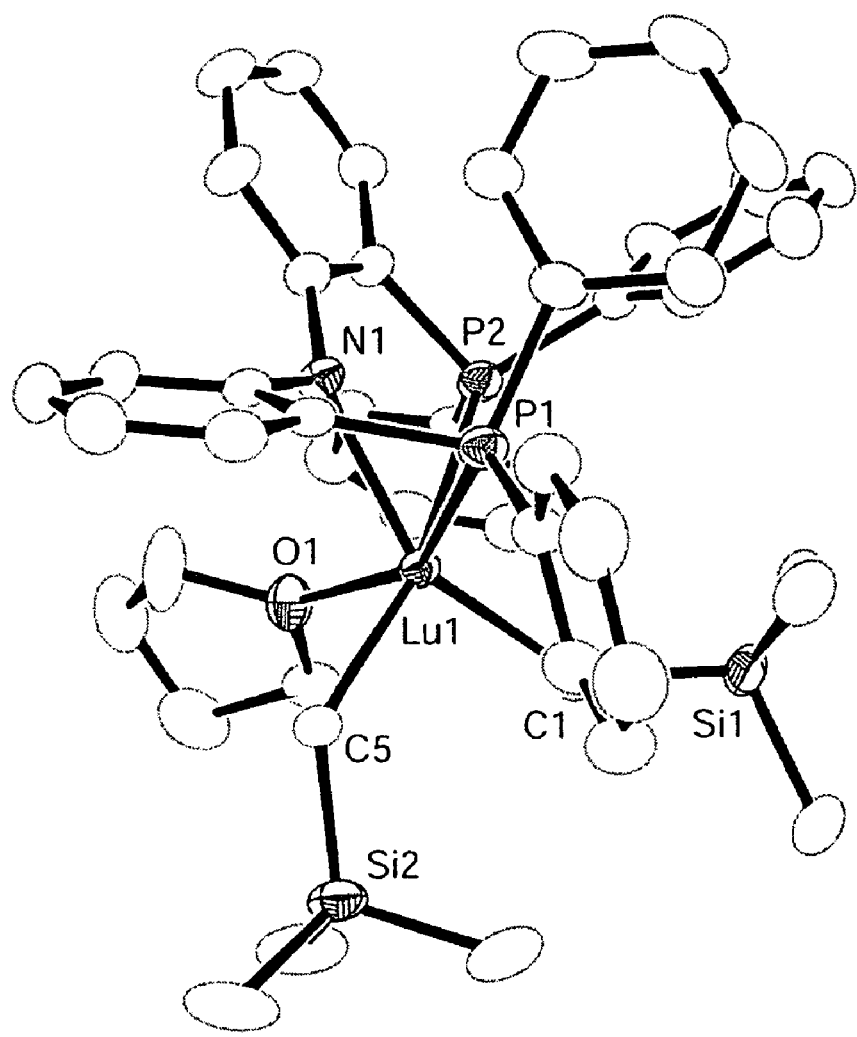

[Figure 4]
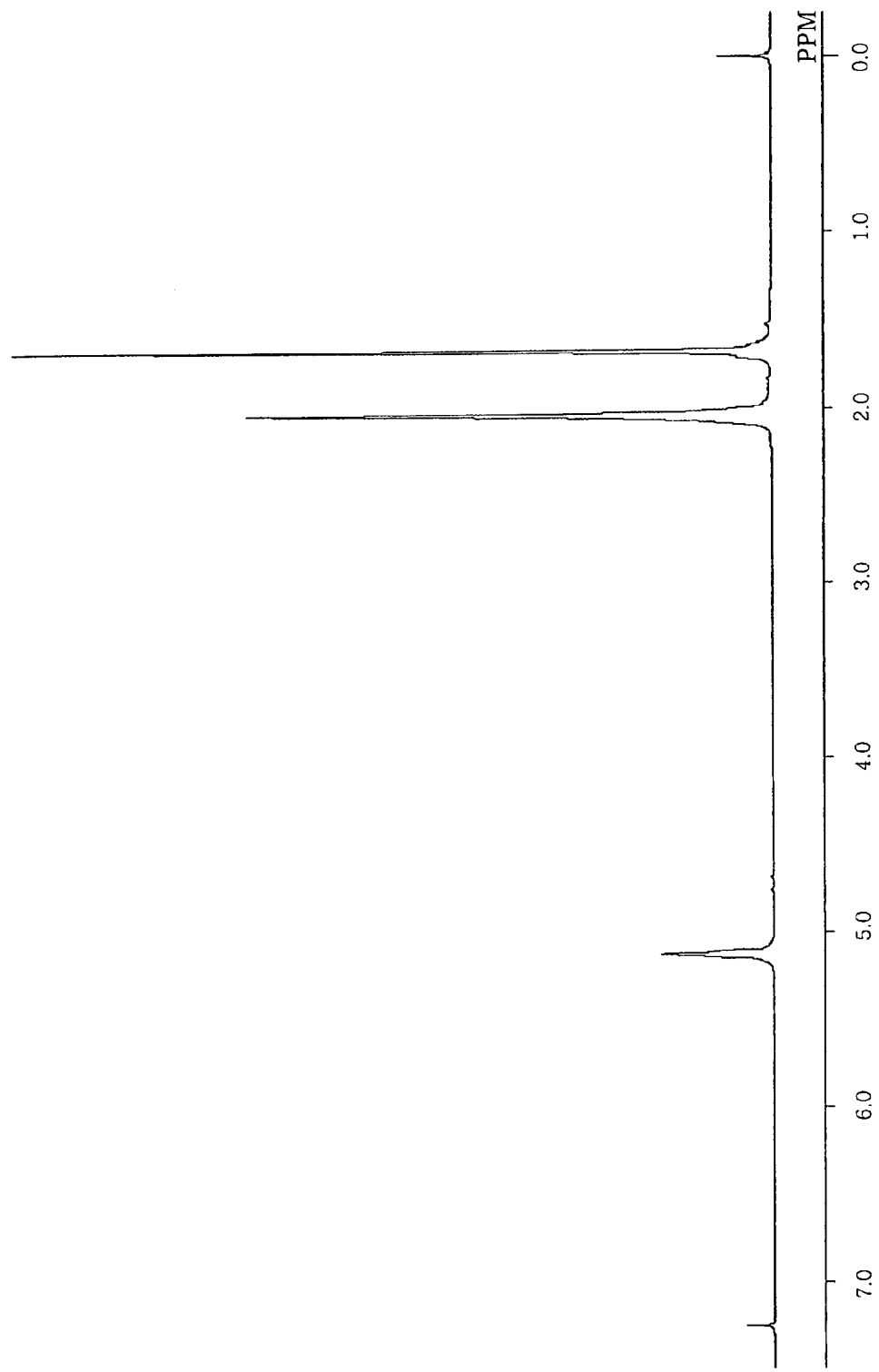

[Figure 5]
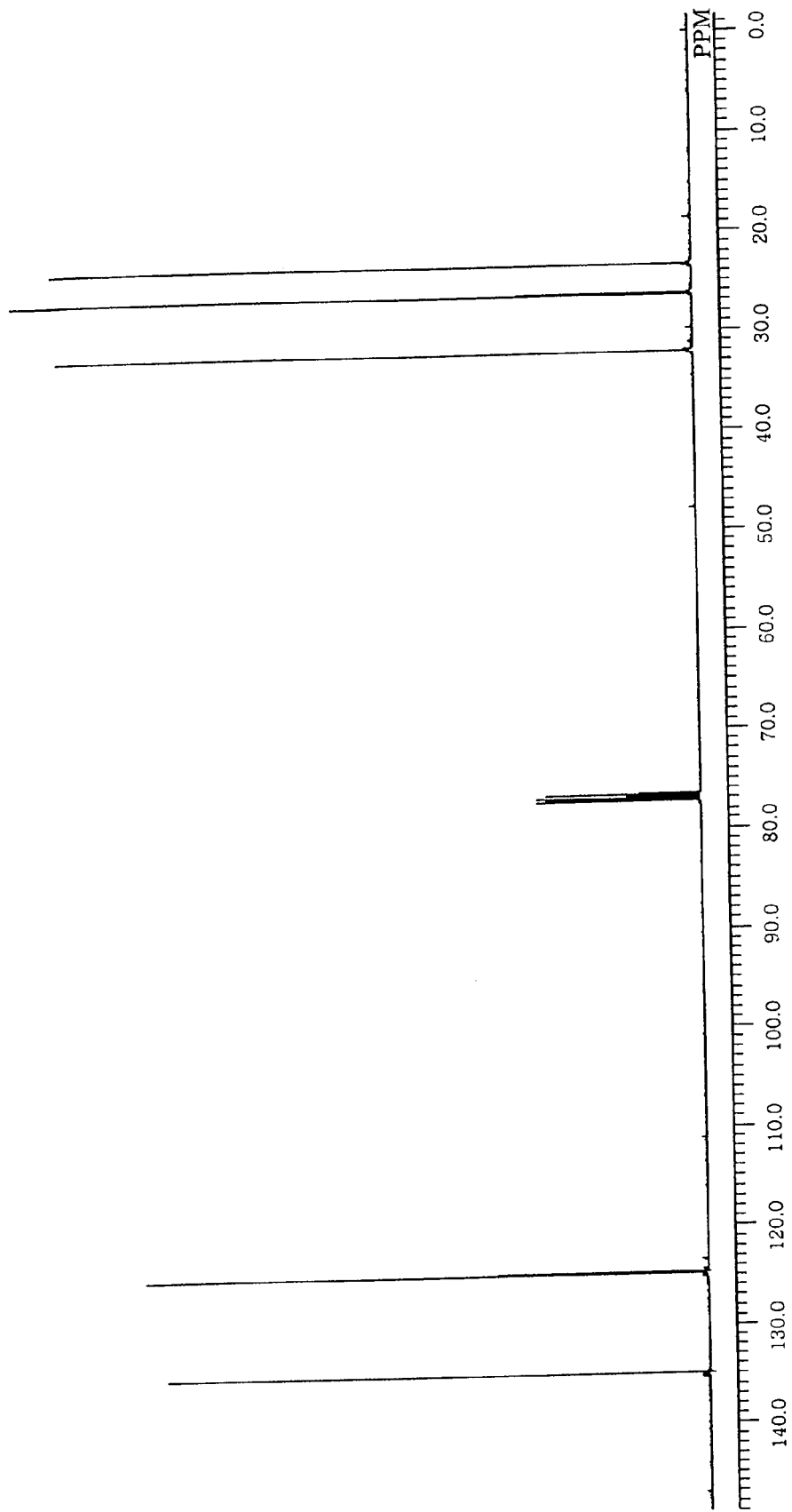

[Figure 6]
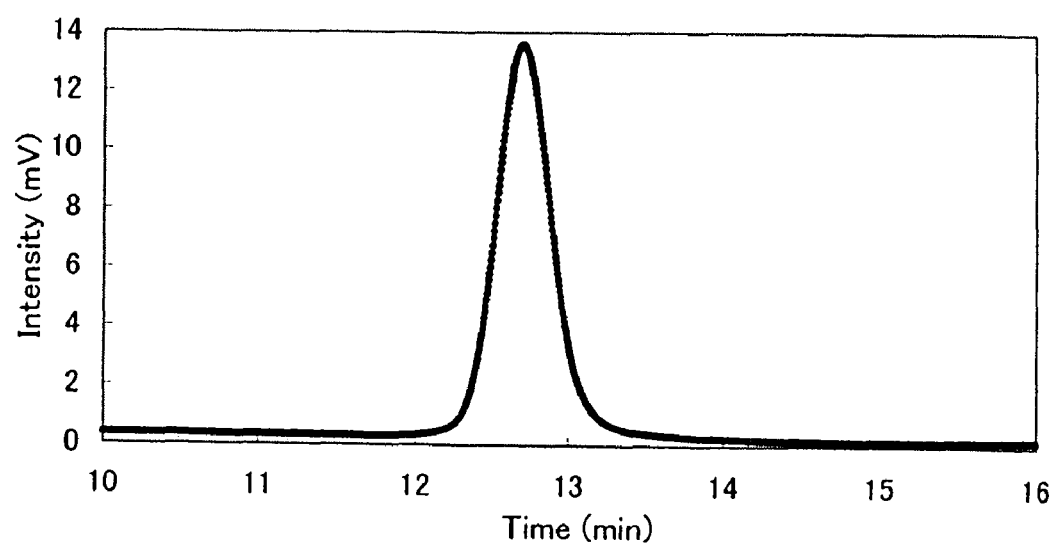

[Figure 7]
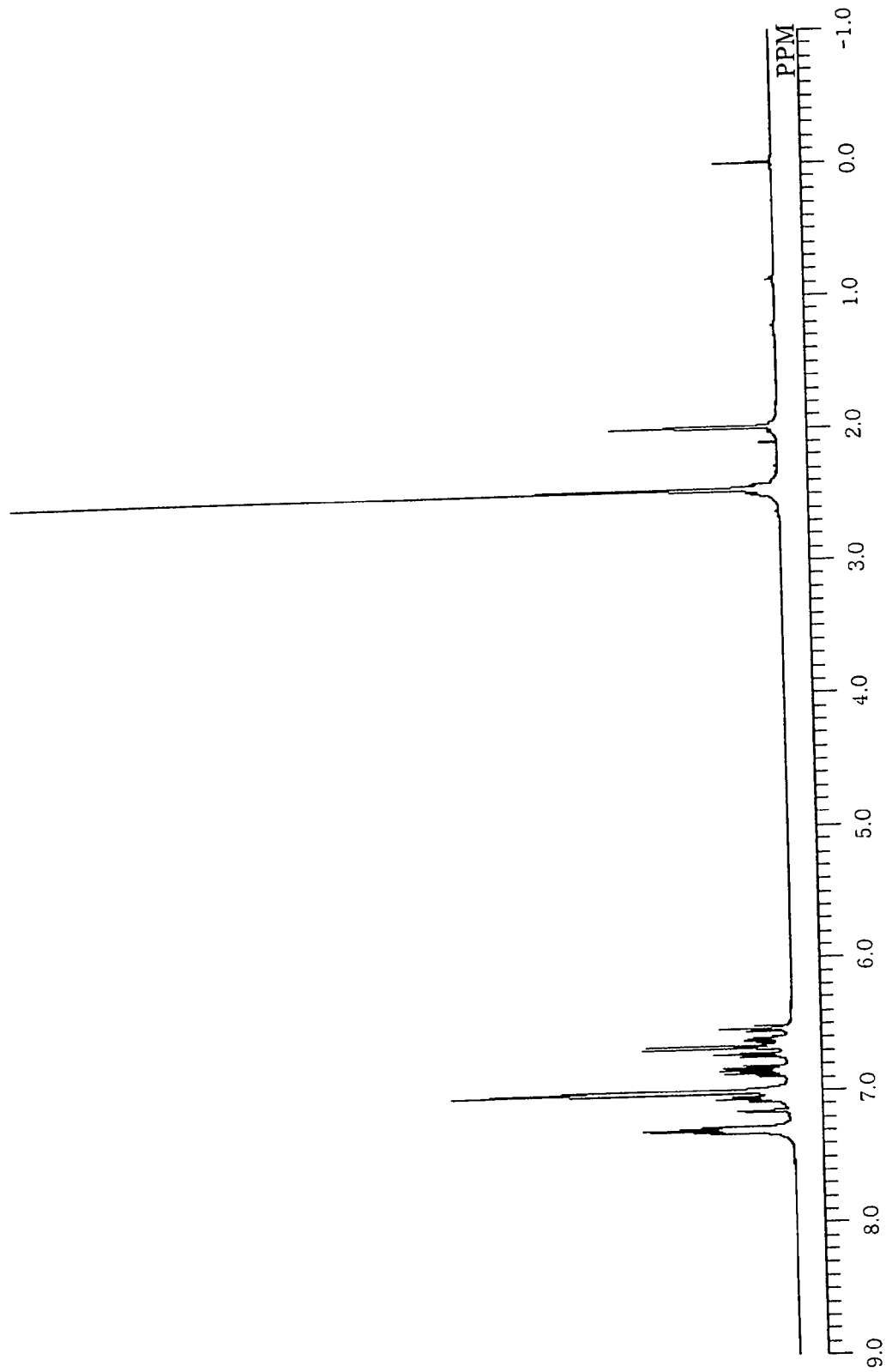

[Figure 8]
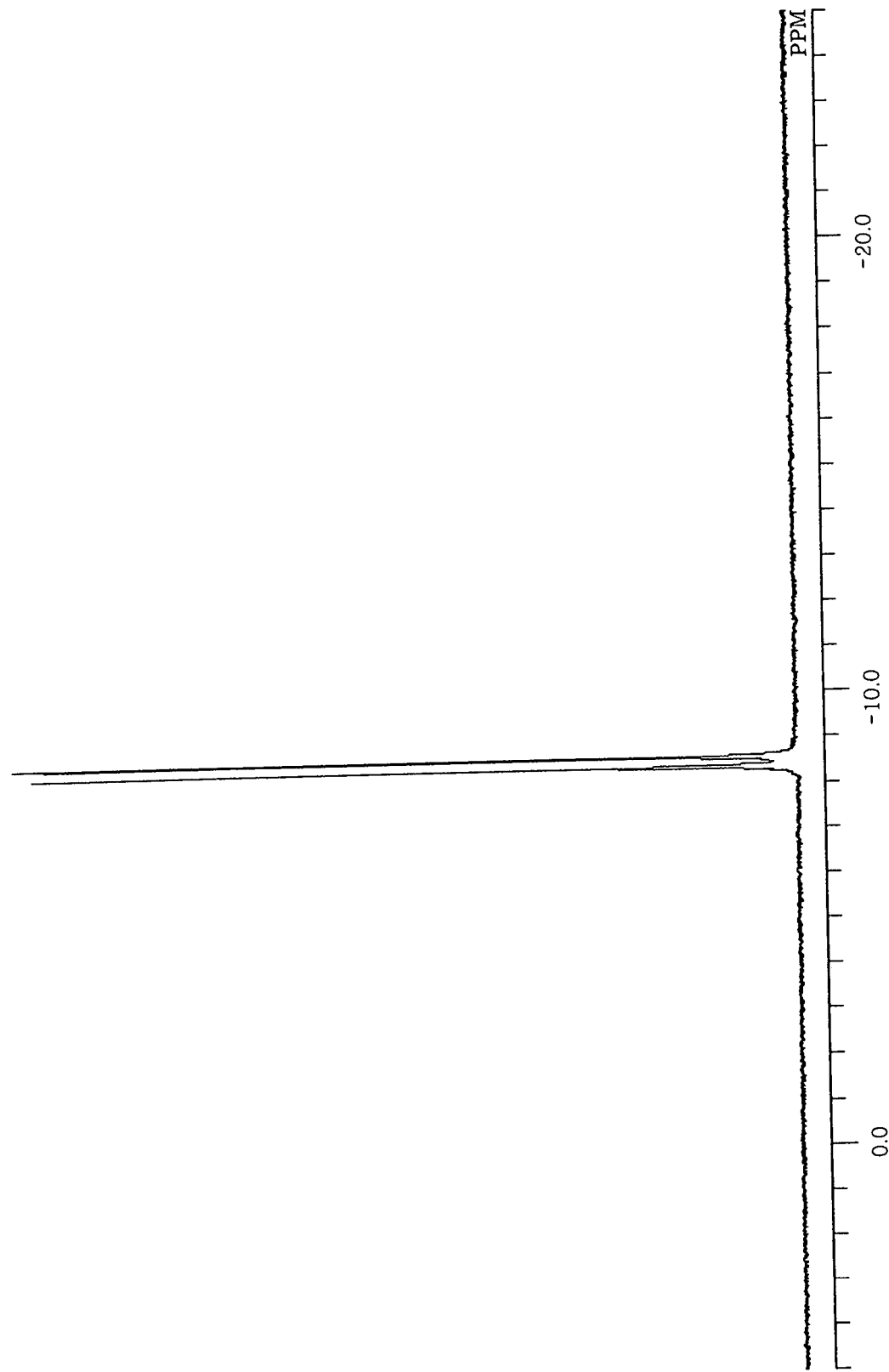

[Figure 9]
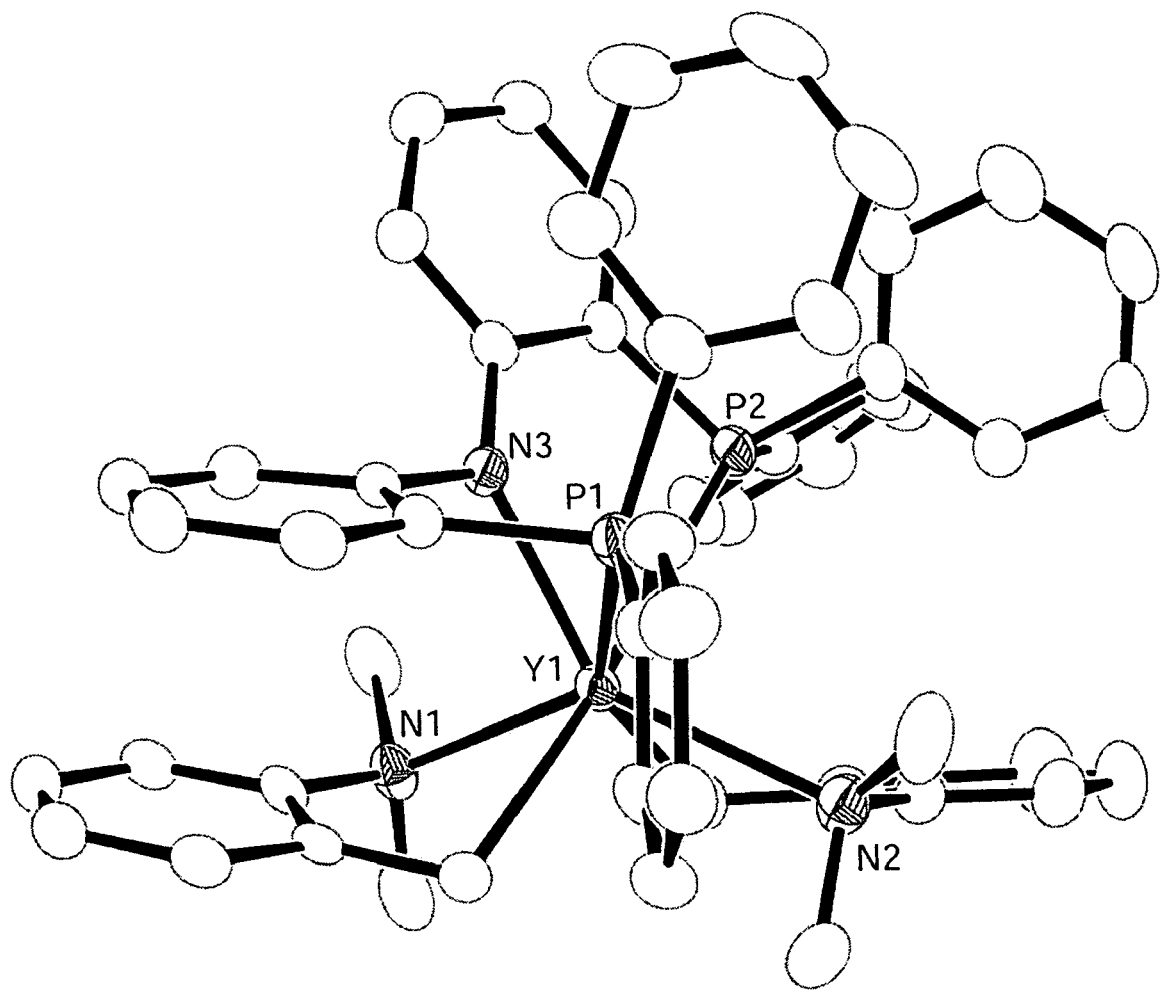

[Figure 10]
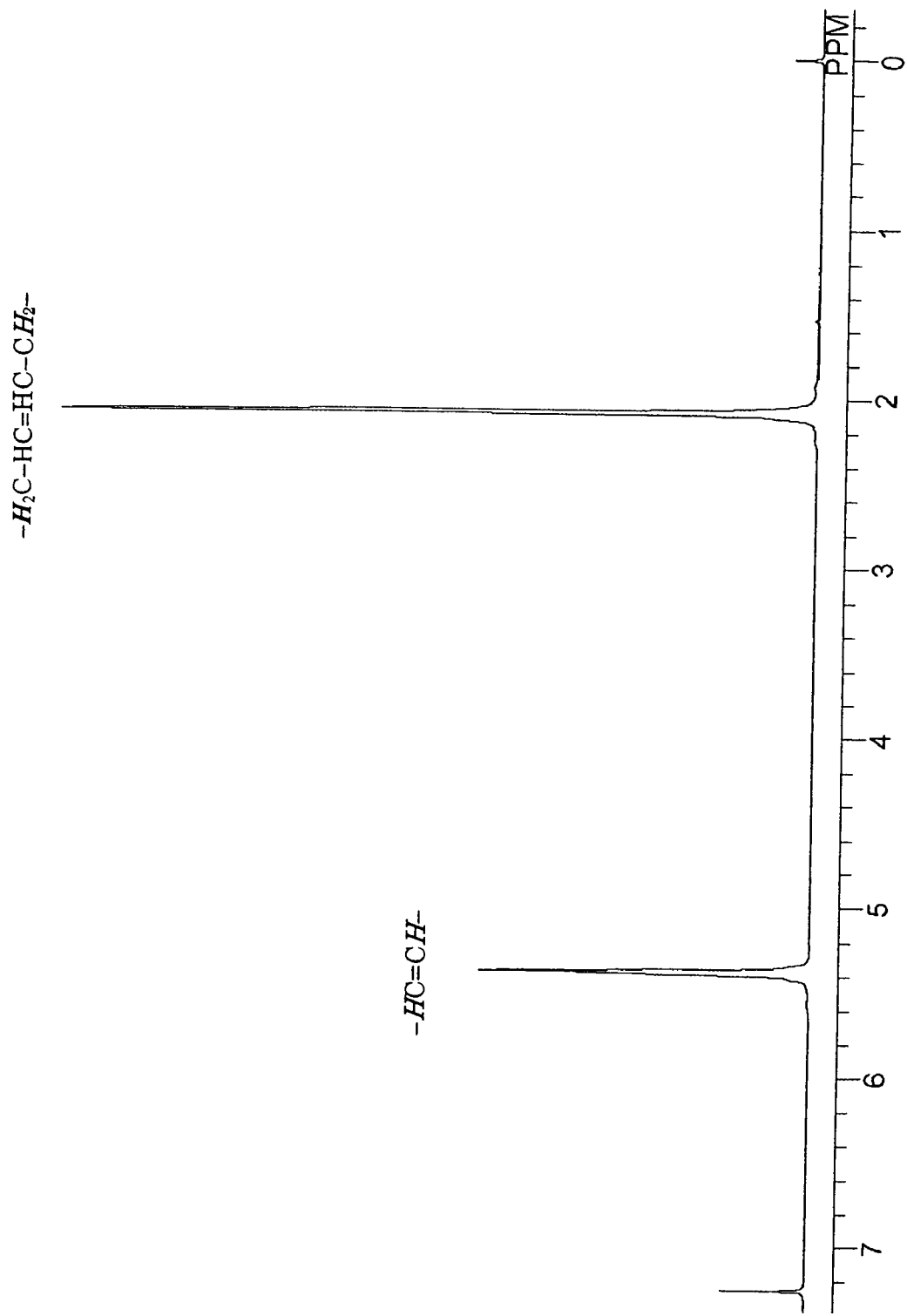

[Figure 11]
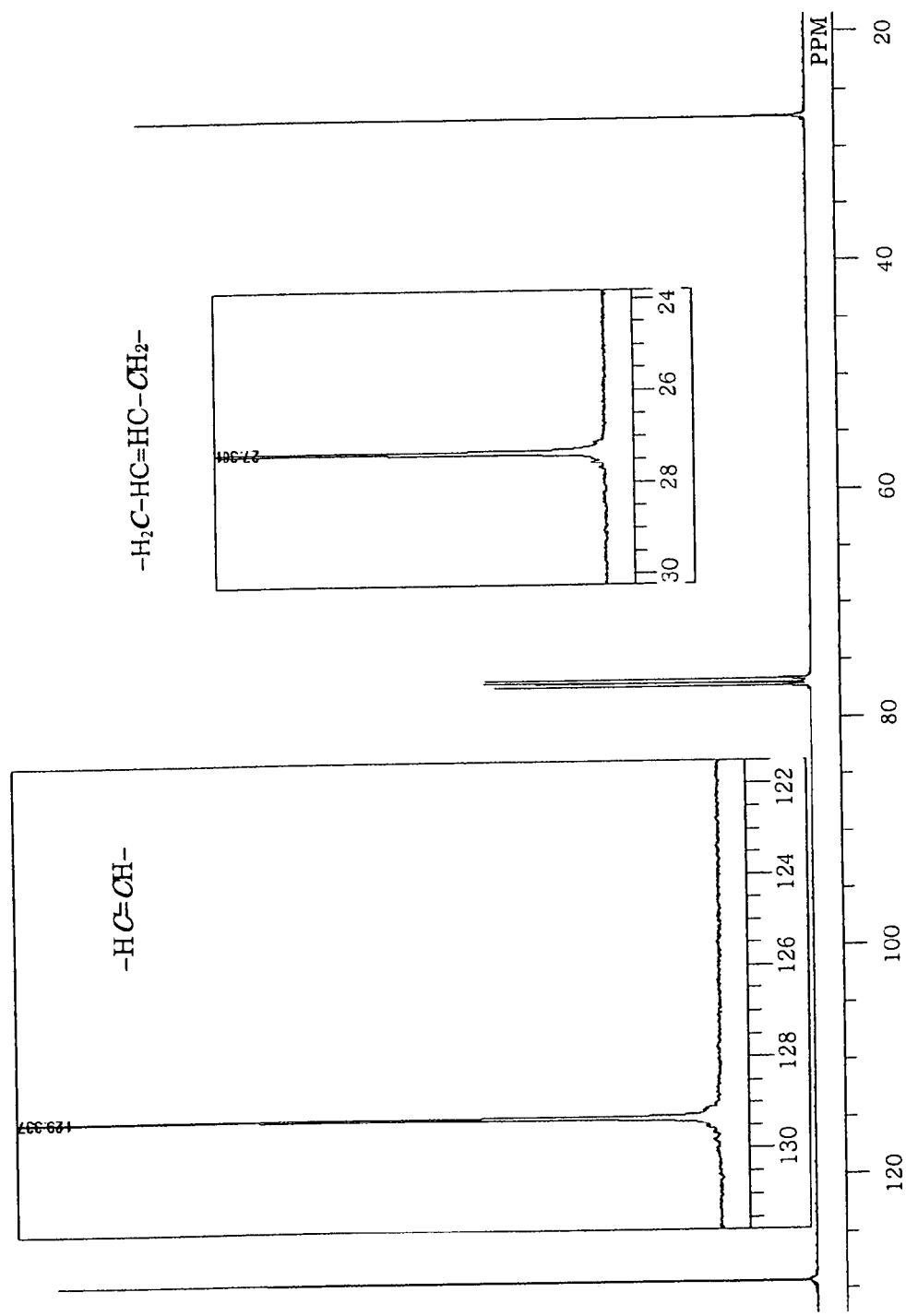

[Figure 12]
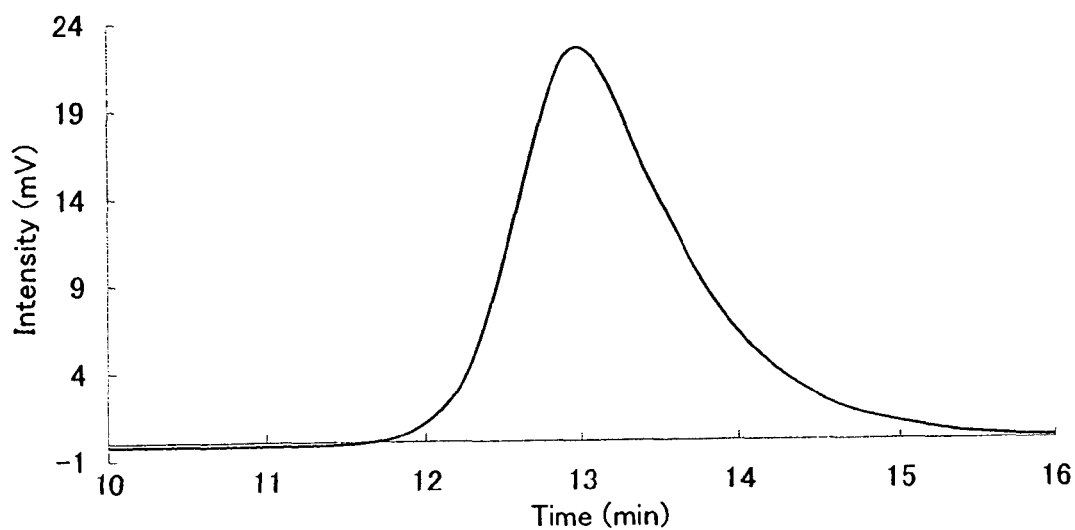
[Figure 13]
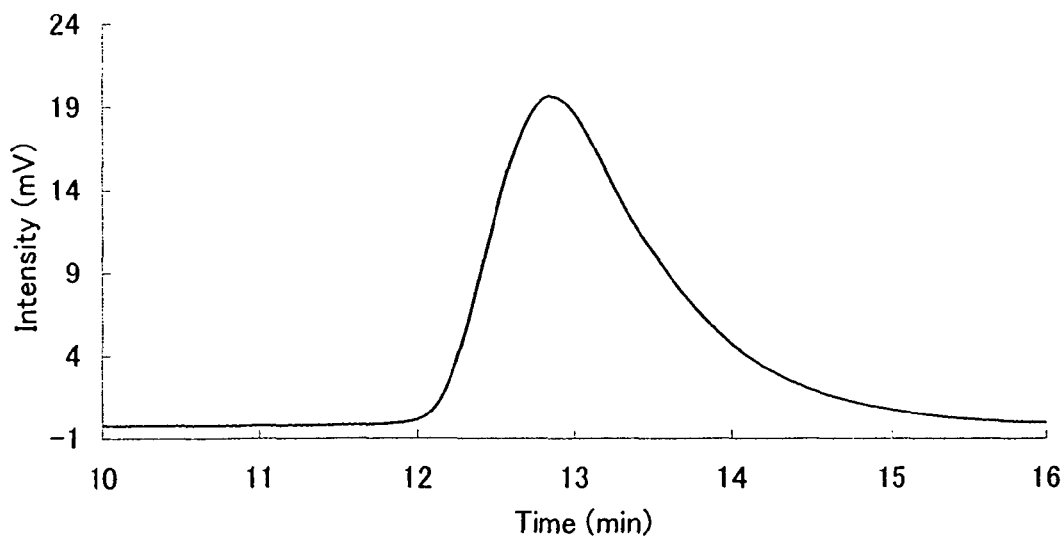

[Figure 14]
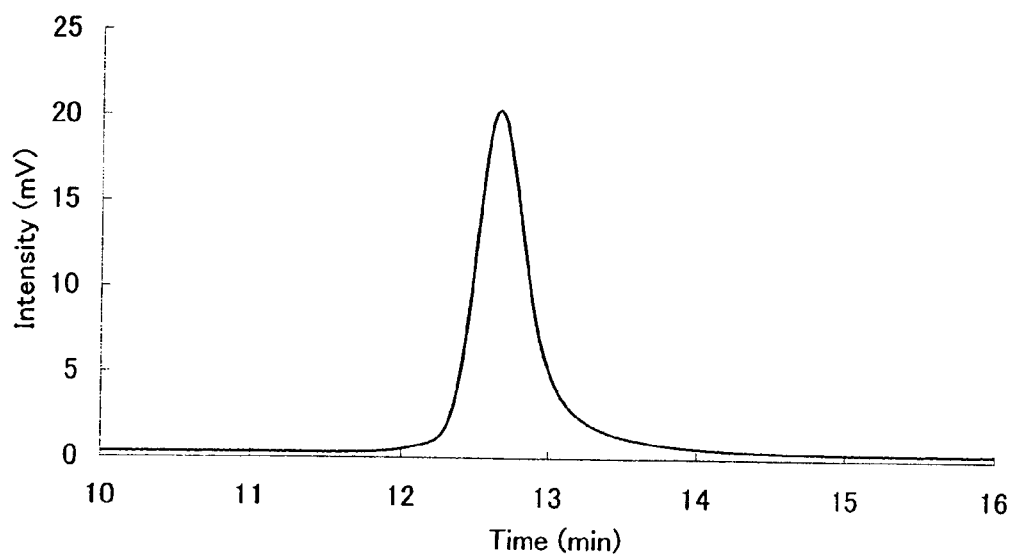
[Figure 15]
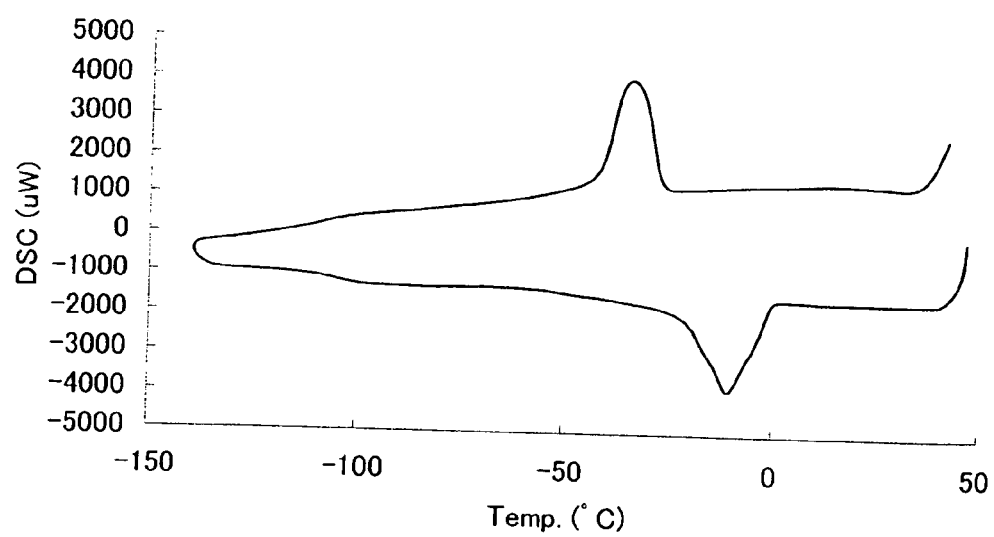

[Figure 16]
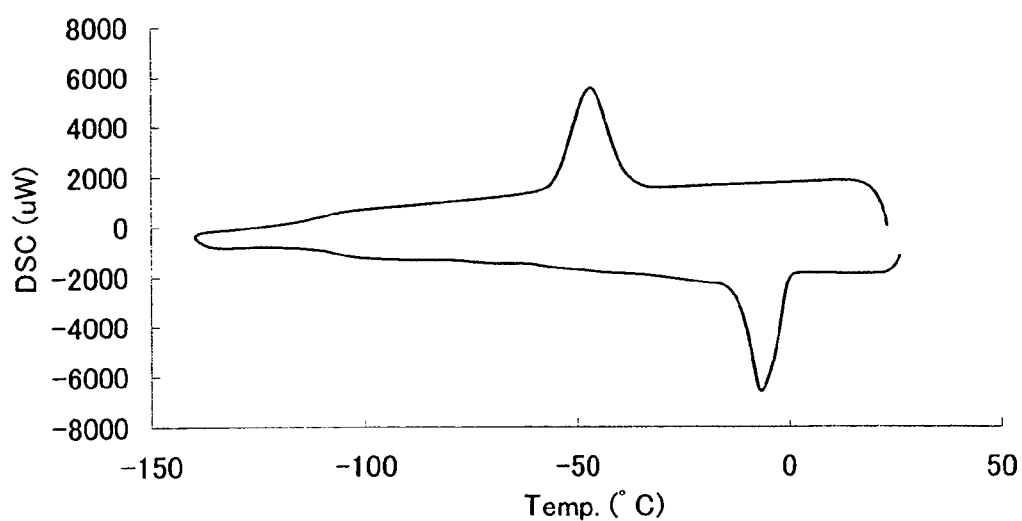

[Figure 17]
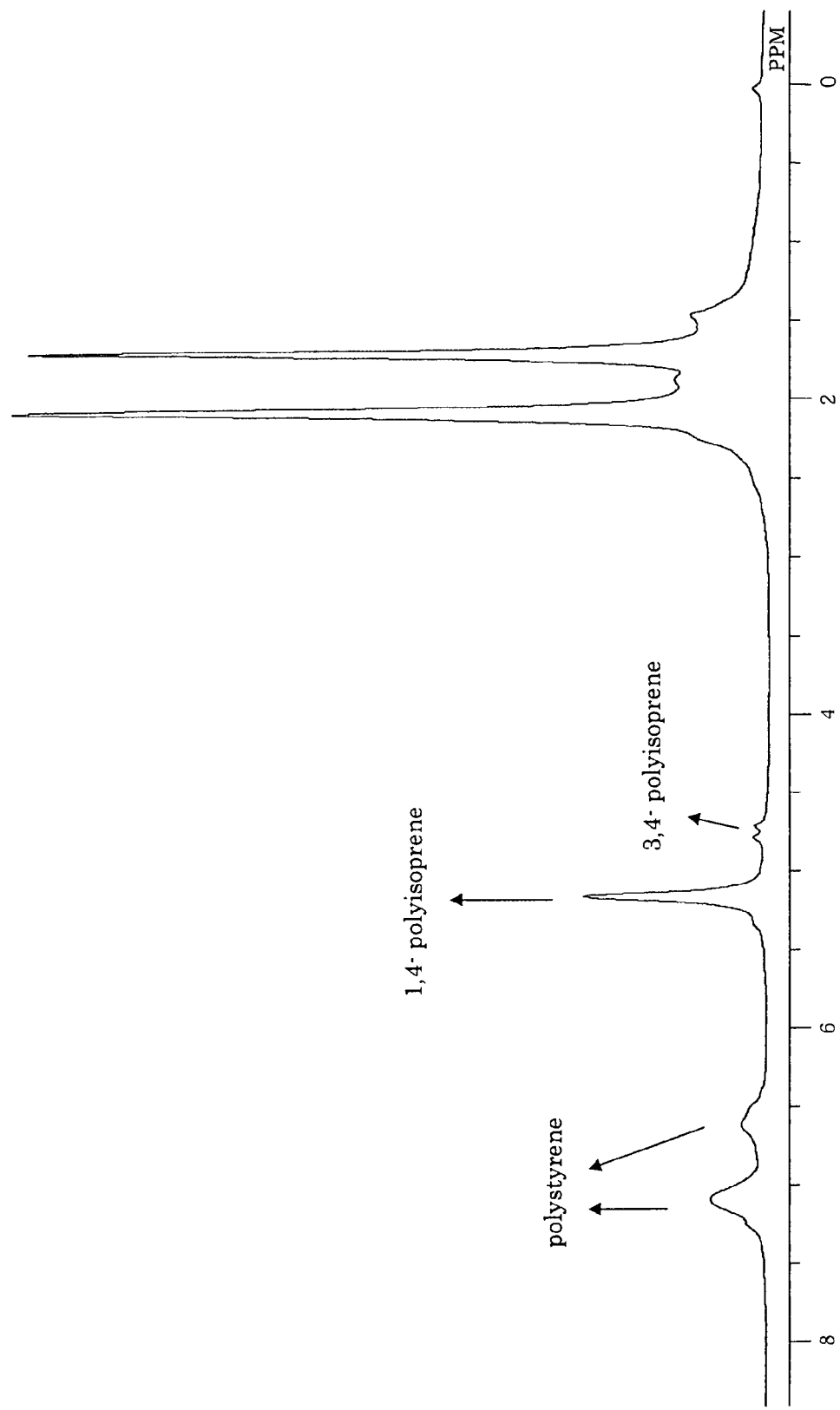

[Figure 18]
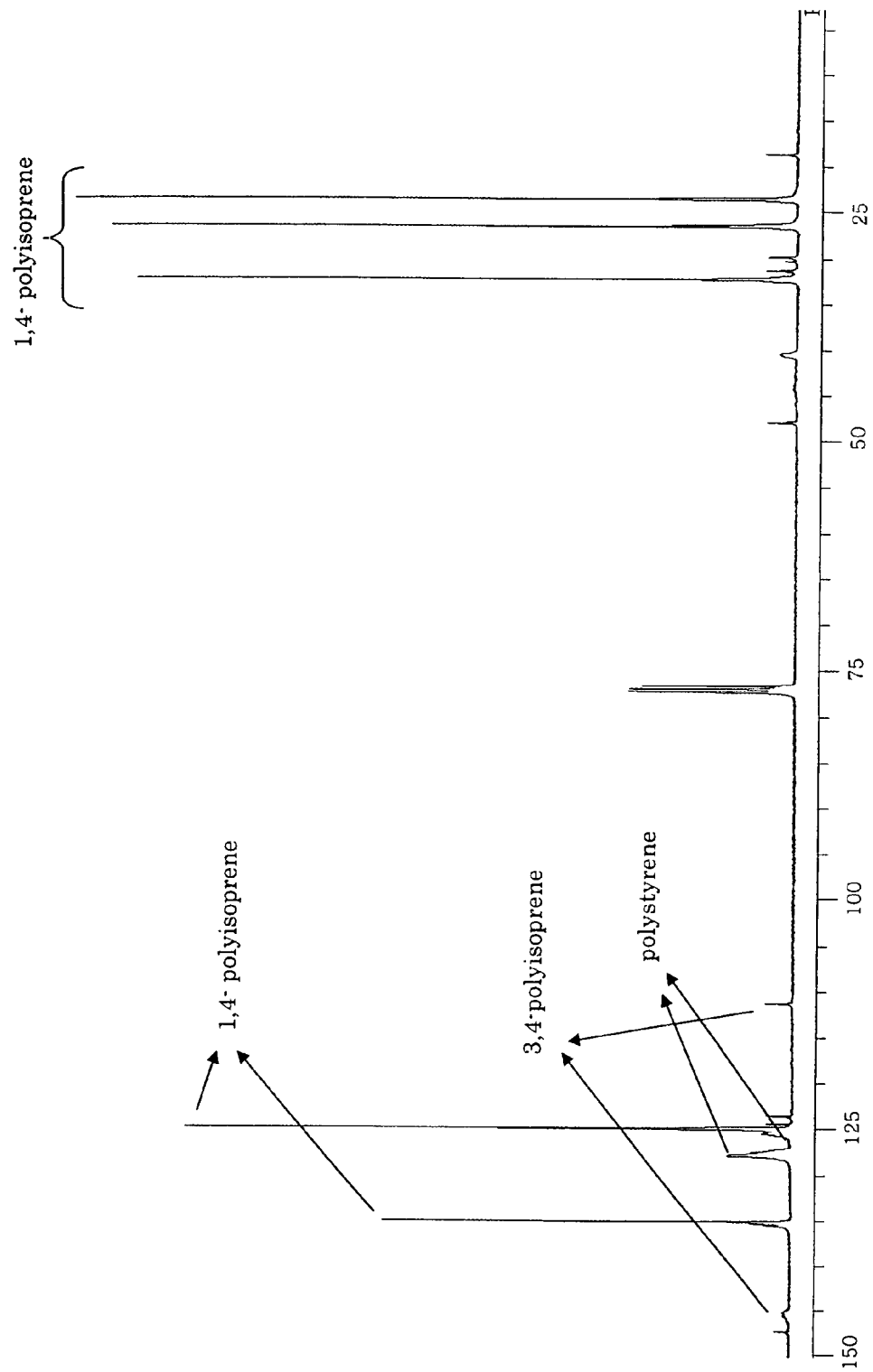

[Figure 19]
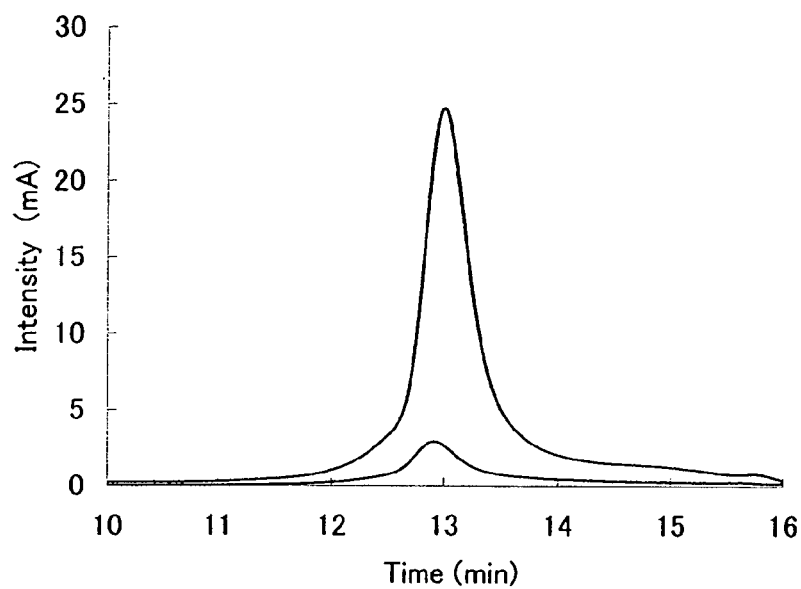
[Figure 20]
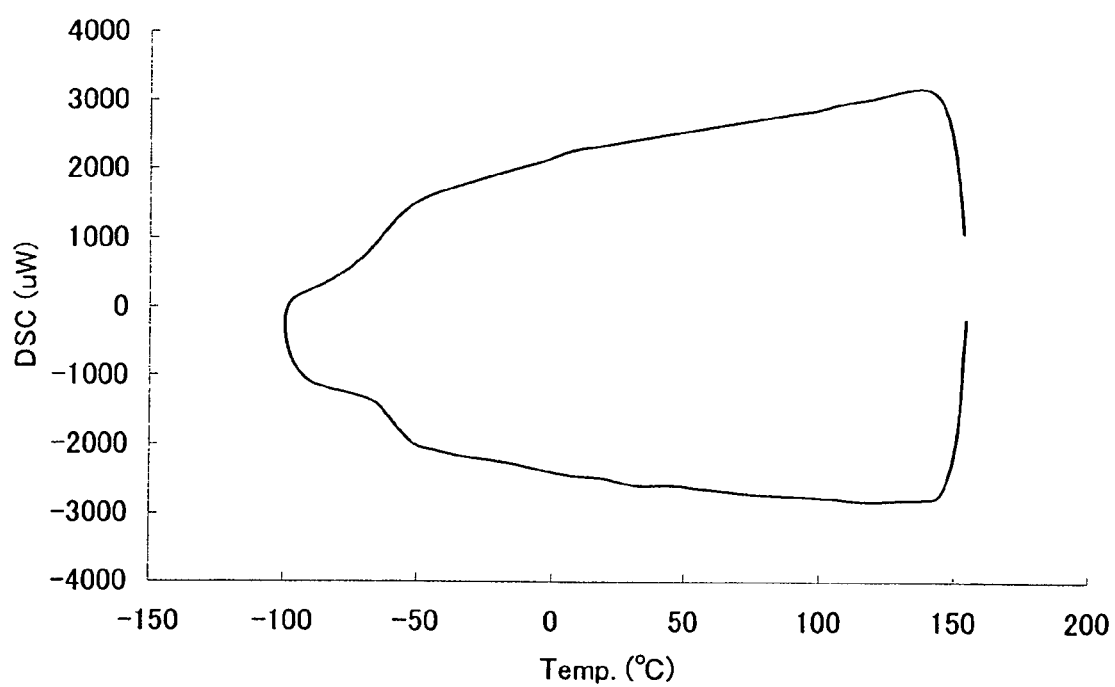

METAL COMPLEX CONTAINING TRIDENTATE LIGAND, AND POLYMERIZATION CATALYST COMPRISING THE SAME

RELATED APPLICATIONS

This application is the national stage of International Application PCT/JP2006/300978, filed Jan. 23, 2006, which in turn claims priority under 35 USC §119 upon Japanese Application No. 2005-014217, filed Jan. 21, 2005.

TECHNICAL FIELD

The present invention relates to a metal complex and a polymerization catalyst composition containing the same. In addition, the present invention relates to an olefin polymer, preferably an isoprene polymer, a butadiene polymer, an isoprene-styrene copolymer, a butadiene-styrene copolymer, a butadiene-isoprene copolymer, and a butadiene-isoprene-styrene copolymer.

BACKGROUND ART

As a metal complex containing an anionic tridentate ligand, which does not belong to a cyclopentadienyl-based one, a complex having the following general formula (A) has been known (see Patent Document 1). It is reported that the metal complex has such a feature that the central metal M which is any transition metal of Groups 4 to 9 and being used as an olefin polymerization catalyst.

[Chem 1]

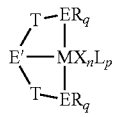

(A)

In addition, as a metal complex containing a tridentate ligand, but not a cyclopentadienyl-based one, a complex having the following general formula (B) has been known (see Non-Patent Document 1). Furthermore, a complex having the following general formula (B') which includes tridante ligand same as tridante ligand of a complex as shown in the formula (B) has also been known (see Non-Patent Document 2).

However, there is no concrete report on reactivity of those metal complexes, and usages of those metal complexes are unknown.

[Chem 2]

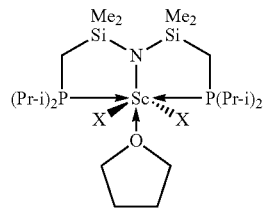

(B)

(In the above formula, X represents chloro, methyl, ethyl, or trimethylsilylmethyl)

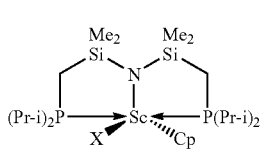

(B')

(In the above formula, X represents chloro, methyl, phenyl, or $BH_4$, and Cp represents a cyclopentadienyl).

Furthermore, as a metal complex containing a tridentate ligand, but not a cyclopentadienyl-based one, a complex represented by the following general formula (C) has also been reported (see Non-Patent Documents 3, 4, and so on). It is known that the reported complex represented by the general formula (C) includes Pd, Ni, Pt, or the like as the central metal M thereof and part of the complex can be used as a catalyst component for the Heck reaction.

[Chem 3]

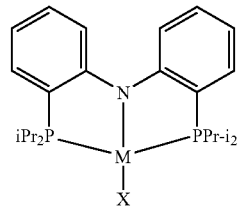

(C)

(In the above formula, M represents Pd, Ni, or Pt and X represents chloro or acetate).

On the other hand, an isoprene polymer, a butadiene polymer, an isoprene-styrene copolymer, a butadiene-styrene copolymer, a butadiene-isoprene copolymer, and so on are used as synthetic rubbers. In particular, a high-cis-1,4-isoprene polymer and a high-cis-1,4-butadiene polymer are synthetic rubbers that have almost the same strengths as those of natural rubbers and are very useful raw materials. Therefore, various investigations have been carried out for the process of producing an isoprene polymer or a butadiene polymer with a high cis-1,4 content. Furthermore, the isoprene polymer with a content of approximately 100% has been also known (see, for example, Patent Document 2 and Non-Patent Document 5).

Furthermore, it has been expected that when a polymer with a sharp molecular-weight distribution and a high-cis-1, 4-isoprene polymer or a high-cis-1,4-butadiene polymer is produced, a higher-strength rubber can be provided.

Patent Document 1: JP 2002-513823 A
Patent Document 2: JP 2004-513998 A
Non-Patent Document 1: Michael D, Fryzuk et al. Organometallics 1996, 15, 3329-3336.
Non-Patent Document 2: Michael D, Fryzuk et al. Can. J. Chem. 2000, 15, 1003-1012.
Non-Patent Document 3: Mei-Hui Huang et al. Organometallics 2004, 23, 2813-2816.
Non-Patent Document 4: Lei Fan et al. Organometallics 2004, 23, 4778-4787.
Non-Patent Document 5: Shojiro Kaita et al. Macromolecules 2004, 37, 5860-5862.

DISCLOSURE OF THE INVENTION

1. The present invention has an object to provide a novel metal complex having a mono-anionic tridentate ligand, but not a cyclopentadienyl one, and a polymerization catalyst composition containing the complex. Furthermore, the present invention intends to provide a method for producing various polymer compounds (preferably novel polymer compounds) using the polymerization catalyst composition.

2. On the other hand, the present invention has another object of the invention to provide an isoprene polymer, a butadiene polymer, an isoprene-styrene copolymer, a butadiene-styrene copolymer, a butadiene-isoprene copolymer, and a butadiene-isoprene-styrene copolymer, each of which has high-cis-1,4 content in a micro structure and a sharp molecular-weight distribution.

That is, the present invention is as shown below.

Firstly, the present invention is an invention of a complex as follows.

1. A complex comprising a mono-anionic tridentate ligand, represented by the following general formula (I):

[Chem 4]

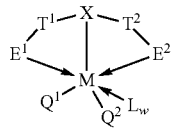

(I)

In the general formula (I),

M represents scandium Sc, yttrium Y, or lanthanoid;

$E^1$-$T^1$-X-$T^2$-$E^2$ represents a mono-anionic tridentate ligand; X represents an anionic electron-donating group containing a ligand atom selected from Group-15 atoms;

$E^1$ and $E^2$ each represent independently a neutral electron-donating group containing a ligand atom selected from one of Group-15 atoms and Group-16 atoms;

$T^1$ and $T^2$ are cross-linking groups that cross-link X with $E^1$ and $E^2$, and each represent independently an arylene group which may have a substituent on an aryl ring;

$Q^1$ and $Q^2$ each represent independently a monoanionic ligand; L represents a neutral Lewis base; and w represents an integral of 0 to 3.

2. The complex according to claim 1, wherein each of the $T^1$ and $T^2$ in the general formula (I) is a phenylene group which may have a substituent on a phenyl ring.

3. The complex according to claims 1 or 2, wherein the M in the general formula (I) is scandium Sc, yttrium Y, lutetium Lu, or lanthanum La.

4. The complex according to any one of claims 1 to 3, wherein the X in the general formula (I) is N.

5. The complex according to any one of claims 1 to 4, wherein the $E^1$ and $E^2$ in the general formula (I) each represent independently a diaryl phosphino group, a dialkyl phosphino group, or an alkylaryl phosphino group.

6. A complex represented by the following general formula (II):

[Chem 5]

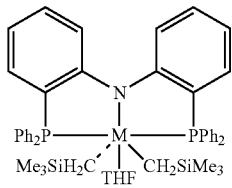

(II)

In general formula (II), M represents scandium Sc, yttrium Y, lutetium Lu, or lanthanum La.

7. A complex represented by the following general formula (III):

[Chem 3]

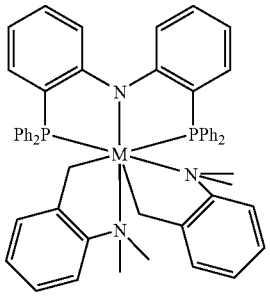

(III)

In general formula (III), M represents scandium Sc, yttrium Y, lutetium Lu, or lanthanum La.

Secondary, the present invention is the invention of a polymerization catalyst composition as follows.

8. A polymerization catalyst composition, comprising the complex according to any one of claims 1 to 7.

9. The polymerization catalyst composition according to claim 8, further comprising a catalyst activator.

10. The polymerization catalyst composition according to claim 9, wherein the catalyst activator is an ionic compound made of a non-coordination anion and a cation.

11. The polymerization catalyst composition according to claim 10, wherein the non-coordination anion is a quadrivalent boron anion.

12. The polymerization catalyst composition according to any one of claims 8 to 11, which is used for polymerization of olefin.

13. The polymerization catalyst composition according to claim 12, wherein the olefin is at least one of isoprene, butadiene, or styrene.

14. A process for producing a polymer, comprising: polymerizing additional polymerizable monomers utilizing the polymerization catalyst composition according to any one of claims 8 to 13.

Thirdly, the present invention is the invention of a polymer as follows.

15. The process according to claim 14, wherein the additional polymerizable monomer is olefin, and the polymer is an olefin polymer.

16. The process according to claim 15, wherein:

the additional polymerizable monomer is at least one of isoprene, butadiene, or styrene; and the polymer is an isoprene polymer, a butadiene polymer, a styrene polymer, a butadiene-isoprene copolymer, a butadiene-styrene copolymer, an isoprene-styrene copolymer, or a butadiene-isoprene-styrene copolymer.

Fourthly, the present invention is the invention of a polymer as follows.

17. A conjugated diene polymer, obtained by polymerizing conjugated diene monomers utilizing the polymerization catalyst composition according to any one of claims 8 to 13, wherein:

the cis-1,4 content of a micro structure is 90% or more with respect to all of conjugated diene monomer structural units; and an index of molecular weight distribution, Mw/Mn, is 2.0 or less.

18. The conjugated diene polymer according to claim 17, wherein the conjugated diene monomer is at least one of butadiene or isoprene.

19. A conjugated diene polymer, having a cis-1,4 content of a micro structure of 90% or more with respect to all of conjugated diene monomer structural units, and having an index of molecular weight distribution, Mw/Mn of 2.0 or less.

20. An isoprene polymer, having a cis-1,4 content of a micro structure of the polymer of 90% or more, and having an index of molecular weight distribution, Mw/Mn of 1.5 or less.

21. An butadiene polymer, having a cis-1,4 content in a micro structure of the polymer of 90% or more, and having an index of molecular weight distribution, Mw/Mn of 1.3 or less.

22. An isoprene-styrene copolymer, having an isoprene content of 5 to 95% in weight percent, having a cis-1,4 content in a micro structure of 90% or more with respect to all of isoprene structural units, and having an index of molecular weight distribution, Mw/Mn of 2.0 or less.

BRIEF DESCRIPTION OF THE DRAWINGS

FIG. 1 is a $^1$H-NMR spectrum chart of a complex obtained in Example 1, where a measurement is conducted using heavy benzene as a solvent at room temperature.

FIG. 2 is a $^{31}$P-NMR spectrum chart of the complex obtained in Example 1, where a measurement is conducted using heavy benzene as a solvent at room temperature.

FIG. 3 is an ORTEP diagram of a complex [Lu(CH$_2$SiMe$_3$)$_2$(PNP)(thf)] obtained in Example 3.

FIG. 4 is a $^1$H-NMR spectrum chart of an isoprene polymer obtained in Example 4, where a measurement is conducted using heavy chloroform as a solvent at room temperature.

FIG. 5 is a $^{13}$C-NMR spectrum chart of the isoprene polymer obtained in Example 4, where a measurement is conducted using heavy chloroform as a solvent at room temperature.

FIG. 6 is a GPC chart of the isoprene polymer obtained in Example 4.

FIG. 7 is a $^1$H-NMR spectrum chart of a complex [Y(CH$_2$C$_6$H$_4$NMe$_2$-o)$_2$(PNP)] obtained in Example 12, where a measurement is conducted using heavy benzene at room temperature.

FIG. 8 is a $^{31}$P-NMR spectrum chart of the complex [Y(CH$_2$C$_6$H$_4$NMe$_2$-o)$_2$(PNP)] obtained in Example 12, where a measurement is conducted using heavy benzene at room temperature.

FIG. 9 is an ORTEP diagram of the complex [Y(CH$_2$C$_6$H$_4$NMe$_2$-o)$_2$(PNP)] obtained in Example 12.

FIG. 10 is a $^1$H-NMR spectrum chart of a butadiene polymer obtained in Example 32, where a measurement is conducted using heavy chloroform as a solvent at room temperature.

FIG. 11 is a $^{13}$C-NMR spectrum chart of the butadiene polymer obtained in Example 32, where a measurement is conducted using heavy chloroform as a solvent at room temperature.

FIG. 12 is a GPC chart of a butadiene polymer obtained in Example 27.

FIG. 13 is a GPC chart of a butadiene polymer obtained in Example 28.

FIG. 14 is a GPC chart of a butadiene polymer obtained in Example 30.

FIG. 15 is a DSC chart of the butadiene polymer obtained in Example 28.

FIG. 16 is a DSC chart of the butadiene polymer obtained in Example 30.

FIG. 17 is a $^1$H-NMR spectrum chart of an isoprene-styrene copolymer obtained in Example 34, where a measurement is conducted using heavy chloroform as a solvent at room temperature.

FIG. 18 is a $^{13}$C-NMR spectrum chart of an isoprene-styrene copolymer obtained in Example 34, where a measurement is conducted using heavy chloroform as a solvent at room temperature.

FIG. 19 is a GPC chart of the isoprene-styrene copolymer obtained in Example 34.

FIG. 20 is a DSC chart of the isoprene-styrene copolymer obtained in Example 34.

BEST MODE FOR CARRYING OUT THE INVENTION (1. Complex of the Present Invention)

The complex of the present invention contains the central metal M such as a group-3 metal atom or a lanthanoid metal atom, a mono-anionic tridentate ligand, monoanionic ligands Q$^1$ and Q$^2$, and neutral Lewis base L in the number of w, and is represented by the following general formula (I):

[Chem 7]

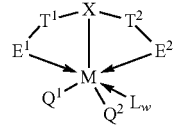

(I)

In the general formula (I), the central metal M may be a group-3 metal atom or a lanthanoid metal but not specifically limited thereto. The complex of the present invention can be used as a component of a polymerization catalyst composition, so the central metal M can be suitably selected according to the kind of a monomer to be polymerized and examples thereof preferably include scandium Sc, yttrium Y, lutetium Lu, gadolinium Gd, praseodymium Pr, neodymium Nd, and lanthanum La, more preferably, Sc, Y, Lu, and La. In addition, the oxidation number of the central metal M is 3.

In the general formula (I), E$^1$-T$^1$-X-T$^2$-E$^2$ represents a mono-anionic tridentate ligand. E$^1$ and E$^2$ represent neutral electron-donating groups, X represents an anionic electron-donating group, where each of them occupies the coordination position of the central metal M. In addition, T$^1$ and T$^2$ are groups that cross-link anionic electron-donating groups X with neutral electron-donating groups E$^1$ and E$^2$, respectively.

The neutral electron-donating groups E$^1$ and E$^2$ are groups that contain ligand atoms selected from Group 15 and Group 16, respectively. In addition, E$^1$ and E$^2$ may be an identical group or may be different groups. Examples of the ligand atom include nitrogen N, phosphorus P, oxygen O, and sulfur S, but preferably P.

When the ligand atoms included in any of the above-mentioned E$^1$ and E$^2$ is P, examples of the neutral electron-donating group E$^1$ or E$^2$ include: (1) diaryl phosphino groups such as a diphenyl phosphino group and a ditolylphosphino group; (2) dialkylphosphino groups such as a dimethylphosphino group and a diethylphosphino group; and (3) alkylaryl phosphino groups such as a methylphenyl phosphino group, more preferably a diarylphosphino group.

When the ligand atom in any of the E$^1$ and E$^2$ is N, examples of the neutral electron-donating group E$^1$ or E$^2$ include: (1) dialkyl amino groups such as a dimethyl amino group, a diethyl amino group, and a bis(trimethylsilyl) amino group; (2) diaryl amino groups such as a diphenyl amino group; and (3) alkylaryl amino groups such as a methyl phenyl group.

When the ligand atom in any of the $E^1$ and $E^2$ is O, examples of the neutral electron-donating group $E^1$ or $E^2$ include: (1) alkoxy groups such as a methoxy group, an ethoxy group, a propoxy group, and a butoxy group; and (2) aryloxy groups such as a phenoxy group and a 2,6-dimethylphenoxy group.

When the ligand atom in any of the $E^1$ and $E^2$ is S, examples of the neutral electron-donating group $E^1$ or $E^2$ include: (1) alkyl thio groups such as a methylthio group, an ethylthio group, a propylthio group, and a butylthio group; and (2) arylthio groups such as a phenylthio group and a tolylthio group.

Furthermore, $E^1$ and $E^2$ may be heterocyclic groups which include ligand atom selected from Group 15 or Group 16, respectively. The heterocyclic groups include a furyl group, a benzofuryl group, a thienyl group, a benzothienyl group, a pyrazolyl group, a triazolyl group, a tetrazolyl group, a pyridyl group, an imidazolyl group, a benzo imidazolyl group, indolyl group, an indazolyl group, a quinolyl group, an isoquinolyl group, an oxazolyl group, and a thiazolyl group.

The anionic electron-donating group X is a group containing a ligand atom selected from Group 15. Examples of the ligand atom may be preferably given as phosphorus P or nitrogen N, more preferably N.

The cross-linking groups $T^1$ and $T^2$ may be groups capable of cross-linking $E^1$ and $E^2$ with X, respectively. Among them, an arylene group can be exemplified. In addition, $T^1$ and $T^2$ may be the identical group or different groups.

The above arylene group can be a phenylene group, a naphthylene group, a pyridilene group, a thienylene group, or the like, preferably a phenylene group or a naphthylene group. In addition, on the aryl ring of the above arylene group, any group may be substituted. The substituents include: alkyl groups such as a methyl group and an ethyl group; aryl groups such as a phenyl group and a tolyl group; halogeno groups such as fluoro, chloro, and bromo; and sylyl groups such as a trimethylsylyl group.

As the above-mentioned arylene group, more preferably, a 1,2-phenylene group can be exemplified.

Examples of the monoanionic tridentate ligand in the complex of the present invention preferably include those represented below. They can be produced with reference to a producing process example as described below, the publication of Organometallics,23,p4778-4787(2004), or the like.

[Chem 8]

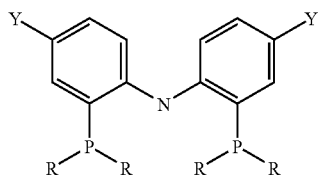

(In the above formula, R represents an alkyl group or an aryl group, Y represents a hydrogen, an alkyl group, a halogeno group, a silyl group, or the like).

In the above general formula (I), $Q^1$ and $Q^2$ are monoanionic ligands. Examples of monoanionic ligands include: (1) hydride; (2) halide; (3) a substitute or unsubstitute hydrocarbyl group having 1 to 20 carbon atoms; (4) a substitute or unsubstitute alkoxy or aryloxy group having 1 to 20 carbon atoms; (5) a substitute or unsubstitute amide group having 1 to 20 carbon atoms (including a silylamide group); and (6) a phosphino group, and the hydrocarbyl group is preferably exemplified, but not specifically limited to these examples.

$Q^1$ and $Q^2$ may be coupled with each other or may be combined to form a dianionic ligand. Examples of the dianionic ligand include alkylidene, diene, a cyclometallated hydrocarbyl group, and a bidentate chelate ligand.

The halide may be any one of the chloride, bromide, fluoride, and iodide.

The hydrocarbyl group having 1 to 20 carbon atoms may be an alkyl group such as a methyl group, an ethyl group, a propyl group, an isopropyl group, a butyl group, an isobutyl group, a t-butyl group, a pentyl group, an amyl group, an isoamyl group, a hexyl group, a cyclohexyl group, a heptyl group, an octyl group, a nonyl group, a decyl group, a cetyl group, a 2-ethylhexyl group, a 2-phenylethynyl group, a 2-(trimethylsilyl)ethynyl group, and a 3,3-dimethyl-1-butynyl group; an unsubstituted hydrocarbyl group such as a phenyl group and a benzyl group; and a substituted hydrocarbyl group such as a trialkylsilylmethyl group, a bis(trialkylsilyl)methyl group, an aminophenyl group, and an aminobenzyl group. Of those, a trialkylsilylmethyl group and an aminobenzyl group are preferred. More preferred example of the trialkylsilylmethyl group includes a trimethylsilylmethyl group.

The alkoxy group or aryloxy group preferably includes a methoxy group and a substituted or unsubstituted phenoxy group. Preferable examples of the amide group include a dimethylamide group, a diethylamide group, a methylethylamide group, a di-t-butylamide group, a diisopropylamide group, an unsubstituted or substituted diphenylamide group, and bis(trimethylsilyl)amide.

Preferable examples of the phosphino group include a diphenylphosphino group, a dicyclohexylphosphino group, a diisopropylphosphino group, a diethylphosphino group, and a dimethylphosphino group.

The alkylidene preferably includes methylidene, ethylidene, propylidene, and benzylidene.

Preferable examples of the cyclometallized hydrocarbyl group include propylene, butylene, pentylene, hexylene, and octylene.

Preferable examples of the diene include 1,3-butadiene, 1,3-pentadiene, 1,4-pentadiene, 1,3-hexadiene, 1,4-hexadiene, 1,5-hexadiene, 2,4-dimethyl-1,3-pentadiene, 2-methyl-1,3-hexadiene, and 2,4-hexadiene.

In the above general formula (I), L denotes a neutral Lewis base. Examples of the neutral Lewis base include tetrahydrofuran (THF), diethyl ether, dimethyl aniline, trimethyl phosphine, and lithium chloride.

In addition, the neutral Lewis base L may be coupled with $Q^1$ and/or $Q^2$ to form a so-called polydentate ligand.

In the general formula (I), w of Lw denotes the number of the neutral Lewis bases. w is different according to the kind of the central metal M, but in general, w is an integral of 0 to 3, preferably 0 or 1.

The complex of the present invention may be a mononuclear complex or may be a polynuclear complex with two or more nuclei.

The complexes of the present invention are particularly preferably those represented by general formulae (II) and (III).

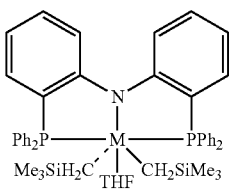

(II)

In the general formula (II), M represents scandium Sc, yttrium Y, lutetium Lu, or lanthanum La.

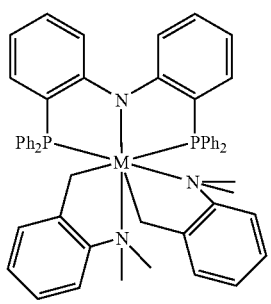

(III)

In the general formula (III), M represents scandium Sc, yttrium Y, lutetium Lu, or lanthanum La.

The complex of the present invention can be produced by the following process using ($MX_3$) or the like as a raw material but not limited to such a process.

(1) A complex in which both $Q^1$ and $Q^2$ are halogen can be obtained by reacting trihalometal ($MX_3$) with a mono-anionic tridentate ligand precursor in the presence of a base. Subsequently, the complex is reacted with alkyl lithium or the like, thereby obtaining the complex of the present invention. Here, for example, the mono-anionic tridentate ligand precursor may be an alkaline salt of $E^1$-$T^1$-X(H)-$T^2$-$E^2$ (e.g., lithium salt).

(2) Trialkyl metal ($MR_3$) is obtained by reacting $MX_3$ with alkyl lithium (RLi). The trialkyl metal is then reacted with the mono-anionic tridentate ligand precursor, thereby obtaining the complex of the present invention. Here, for example, the mono-anionic tridentate ligand precursor may be $E^1$-$T^1$-X(H)-$T^2$-$E^2$.

According to the above-mentioned process (1), the step for removal of alkali halide should be carried out twice. In particular, the removal of alkali halide from the final product is difficult. On the other hand, according to the above-mentioned process (2), there is no alkali halide present in the final product. Thus, the final product can be easily purified.

(2. Polymerization Catalyst Composition of the Present Invention)

The characteristic feature of the polymerization catalyst composition of the present invention is to contain the complex of the present invention as described above, but more preferably characterized by containing a catalyst activator in addition. Alternatively, any of other components may be included. The catalyst activator included in the polymerization catalyst composition of the present invention may be an ionic compound, an alkyl aluminum compound, the Lewis base, or the like, preferably includes an ionic compound.

The above catalyst activator activates the complex of the present invention to exert the activity thereof as a polymerization catalyst. As an activation mechanism, it can be considered that the above complex may react with the catalyst activator and the monoanionic ligand $Q^1$ or $Q^2$ of the complex may be then detached therefrom to generate a cationic complex (active species).

The ionic compound is a compound made of an uncoordinated anion and a cation.

A preferable example of the uncoordinated anion that is a component of an ionic compound includes a tetravalent boron anion such as tetraphenylborate, tetrakis(monofluorophenyl)borate, tetrakis(difluorophenyl)borate, tetrakis(trifluorophenyl)borate, tetrakis(tetrafluorophenyl)borate, tetrakis(pentafluorophenyl)borate, tetratolylborate, tetraxylylborate, pentafluorophenyltriphenylborate, tris(pentafluorophenyl)phenylborate, and triundecahydride-7,8-dicarbaundecaborate.

Of those uncoordinated anions, tetrakis(pentafluorophenyl)borate is preferable.

Examples of the cation that is a component of an ionic compound include a carbonium cation, an oxonium cation, an ammonium cation, a phosphonium cation, a cycloheptatrienyl cation, and a ferrocenium cation having a transition metal.

A specific example of the carbonium cation includes a tri-substituted carbonium cation such as a triphenyl carbonium cation or a tri(substituted-phenyl)carbonium cation. Specific examples of the tri(substituted-phenyl)carbonium cation include a tri(methylphenyl)carbonium cation and a tri(dimethylphenyl)carbonium cation.

Specific examples of the ammonium cation include: a trialkylammonium cation such as trimethylammonium cation, a triethylammonium cation, a tripropylammonium cation, a tributylammonium cation, and tri(n-butyl)ammonium cation; an N,N-dialkylanilinium cation such as an N,N-dimethylanilinium cation, an N,N-diethylanilinium cation, and an N,N-2,4,6-pentamethylanilinium cation; and a dialkylammonium cation such as a diisopropylammonium cation and a dicyclohexylammonium cation.

A specific example of the phosphonium cation includes a triarylphosphonium cation such as a triphenylphosphonium cation, a tri(methylphenyl)phosphonium cation, and a tri(dimethylphenyl)phosphonium cation.

Of those cations, anilinium cation and carbonium cation are preferable, and an N,N-dialkylanilinium cation and triphenylcarbonium cations are more preferable.

Examples of the alkyl aluminum compound include: a trialkyl aluminum such as triethyl aluminum and tributyl aluminum; and an aluminooxane such as MAO and MMAO. Examples of the Lewis acids include $B(C_6F_5)_3$ and $Al(C_6F_5)_3$.

As described above, the polymerization catalyst composition of the present invention is characterized by including both the complex and the catalyst activator. The ratio of a mole content of the catalyst activator to that of the complex in the catalyst composition varies according to the kinds of the complex and the catalyst activator. For instance, when the catalyst activator is an ionic compound, the mole content of the catalyst activator is preferably 0.5 to 5 times, more preferably 1 time that of the complex.

The complex of the present invention reacts with the catalyst activator thereby generating an active species of the catalyst. However, the complex of the present invention may be an active species of the catalyst generated by activating the complex with the catalyst activator.

Here, the term "active species of the catalyst" may be a cation formed by detachment of the monoanionic ligand $Q^1$ or $Q^2$ from the complex. The active species of the catalyst is estimated to, for example, a cation complex having a structure represented by the formula below. In the following formula, $Q^3$ is $Q^1$, $Q^2$ as mentioned-above or a group having one or more monomers between one of $Q^1$ and $Q^2$, and M (in other words, the group where Q is added to one or more monomers).

[Chem 11]

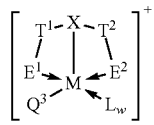

The polymerization catalyst composition of the present invention is used to polymerize various kinds of monomers. A polymerization reaction on which the polymerization catalyst composition of the present invention can act as a catalyst is a polymerization reaction of monomers with addition polymerization characteristics. The addition polymerizable monomers include olefin-based monomers, epoxy-based monomers, isocyanate-based monomers, lactone-based monomers, lactide-based monomers, cyclic carbonate-based monomers, and alkine-based monomers. The polymerization catalyst composition of the present invention is used as a polymerization catalyst preferably for an olefin-based monomer, more preferably for a diene-based polymer, still more preferably for isoprene or butadiene. In addition, it may be used as a polymerization catalyst for styrene.

(3. Process for Producing Polymer of the Present Invention)

The process for producing the polymer of the present invention is characterized by including the step of polymerization of any polymerizable monomer using the polymerization catalyst composition of the present invention described above. In addition, the process for producing the polymer of the present invention can be designed in the same manner as one using the conventional polymerization catalyst utilizing a coordination ion (e.g., Ziegler-Natta catalyst) except for adopting polymerization catalyst composition of the present invention as a polymerization catalyst.

The process for producing the polymer of the present invention includes the step of polymerization of any polymerizable monomer with a vapor phase polymerization method, a solution-polymerization method, a suspension-polymerization method, a liquid phase bulk-polymerization method, an emulsion-polymerization method, a solid-phase-polymerization method, or the like, preferably the step of polymerization with the solution-polymerization method.

The polymerizable monomer to be polymerized by the producing process of the present invention may be any polymerizable monomer, preferably addition polymerizable monomer such as an olefin-based monomer, an epoxy-based monomer, an isocyanate-based monomer, a lactone-based monomer, a lactide-based monomer, a cyclic carbonate-based monomer, or an alkine-based monomer, a combination thereof, more preferably the olefin-based monomer. The olefin-based monomer is preferably a diene-based monomer, more preferably a conjugated diene-based monomer, still more preferably isoprene or butadiene. In addition, styrene may be also preferably used. One of these monomers may be polymerized, or two or more of them may be co-polymerized. For the copolymerization, for example, it is preferable that plurality of kinds of the conjugated diene-based monomers such as isoprene and butadiene, may be used or at least one of the conjugated diene-based monomers may be used together with styrene. Note that, in the present invention, when the term "polymerization" or "polymer" is simply used herein, it may include the meanings of "copolymerization" or "copolymer" according to the monomer to be used.

In particular, for example, it can be carried out by the following procedures:

(1) In a system containing the polymerization catalyst composition of the present invention (preferably a liquid phase system), a polymerizable monomer is supplied to carry out polymerization. Here, when the monomer is in liquid form, it can be supplied by dropping. On the other hand, when it is in gas form, it can be supplied through a gas tube.

(2) In a system containing the polymerizable monomer (preferably a liquid phase system), the polymerization catalyst composition of the present invention can be added or the components of the polymerization catalyst composition can be individually added, thereby allowing the monomer to be polymerized. The catalyst composition to be added may be previously prepared and activated.

When the producing process of the present invention includes a polymerization step by a solution-polymerization method, a solvent used is inactive in a polymerization reaction, and a solvent capable of dissolving the monomer and the catalyst composition can be used. Examples of such a solvent include: saturated aliphatic hydrocarbons such as butane, pentane, hexane, and heptane; saturated alicyclic hydrocarbon such as cyclopentane and cyclohexane; aromatic hydrocarbon such as benzene and toluene; halogenated hydrocarbons such as methylene chloride, chloroform, carbon tetrachloride, trichloro ethylene, perchloroethylene, 1,2-dichloroethane, chlorobenzene, bromobenzene, and chlorotoluene; and ethers such as tetrahydrofuran and diethyl ether.

These solvents may be suitably selected according to the kinds of the complex to be used or the like. Preferable examples of the solvent include: aromatic hydrocarbon such as benzene and toluene; and halogenated hydrocarbons such as methylene chloride, chloroform, carbon tetrachloride, trichloro ethylene, perchloroethylene, 1,2-dichloroethane, chlorobenzene, bromobenzene, and chlorotoluene. Among them, chlorobenzene is more preferably used.

The solvent may be either a single solution or mixed solutions.

The amount of the solvent to be used may be suitably selected according to the kind of the monomer, the composition of the polymerization catalyst composition, or the like.

When the producing process of the present invention includes the polymerization step by the solution-polymerization method, the polymerization reaction may be carried out at any reaction temperature, for example, in the range of −90° C. to 100° C. The reaction temperature may be suitably selected according to the kind of monomer to be polymerized, or the like. In general, however, it can be set to be close to room temperature.

The reaction time in the above-mentioned polymerization reaction may be also suitably selected according to the composition of the polymerization catalyst, so it may be in the range of about several seconds to several hours.

(4. Conjugated Diene-Based Polymer of the Present Invention)

The conjugated diene-based polymer of the present invention is a polymer or a copolymer, which is prepared by polymerization of one kind or two or more kinds of the conjugated diene-based monomers as described above, and characterized by its high cis-1,4 content in its micro structure. The structural unit of the conjugated diene-based polymer can be classified into a cis-1,4 structural unit, a trans-1,4 structural unit, a 3,4 structural unit, a 1,2 structural unit, or the like according to its coupling style. The conjugated diene-based polymer of the present invention means one having a high ratio of the cis-1,4 structural unit to all of the structural units therein. Specifically, the ratio of the cis-1,4 structural unit to the whole structural units is 90% or more, preferably 95% or more. The ratio can be determined from $^1$H-NMR or $^{13}$C-NMR.

The conjugated diene-based polymer of the present invention is not only characterized by its high ratio of the cis-1,4 structural unit to the whole structural units as described above, but also characterized by a small range of its molecular weight distribution (Mw/Mn). The Mw/Mn of the conjugated diene-based polymer of the present invention is generally 2.0 or less. In the conjugated diene-based polymer of the present invention, the small molecular weight distribution means that the Mw/Mn is generally 1.6 or less, preferably 1.5 or less, more preferably 1.3 or less, particularly preferably 1.2 or less.

The molecular weight distribution of the conjugated diene-based polymer of the present invention can be determined by the GPC method. For example, it can be determined by using a GPC-measuring apparatus (TOSOH HLC 8220 GPC, standard substance: polystyrene, eluate: tetrahydrofuran, measured at 40° C.).

The conjugated diene-based polymer of the present invention is characterized in that the ratio of the cis-1,4 structural unit to the whole structural units is high as described above. Besides, it may have a molecular weight distribution (Mw/Mn) of 2.0 or less in general. Preferably, the molecular weight distribution is small. The small molecular weight distribution means that Mw/Mn is 1.6 or less, preferably 1.3 or less, more preferably 1.2 or less.

The molecular weight distribution of the conjugated diene-based polymer of the present invention can be determined by the GPC method. For example, it can be determined by using a GPC-measuring apparatus (TOSOH HLC 8220 GPC, standard substance: polystyrene, eluate: tetrahydrofuran, measured at 40° C.).

A molecular weight of the conjugated diene-based polymer of the present invention is not specifically limited to, but a number average molecular weight Mn thereof is preferably $1 \times 10^4$ or more, more preferably $1 \times 10^5$ or more. The upper limit thereof is also not specifically limited but it may be $1 \times 10^7$ or less.

The number average molecular weight of the conjugated diene-based polymer of the present invention can be determined by the GPC method. Specifically, it can be determined by the same GPC method as the one used in the measurement of the molecular weight distribution as described above.

The conjugated diene-based polymer of the present invention can be produced by polymerization of one or two or more kinds of the conjugated diene-based monomers using the polymerization catalyst composition of the present invention as described above. For instance, one or two or more kinds of conjugated dienes may be polymerized by solution-polymerization with toluene or chlorobenzene as a solvent. The amount of the solvent to be used may be arbitrarily-selected.

The amounts of the complex and the ionic compound to be used in the polymerization are preferably at a mole ratio of about 1:1. In addition, the mole amount of the complex is preferably 0.00001 to 0.01 times higher than that of the conjugated diene-based monomer. The reaction may be carried out at about room temperature and the reaction time period may be about several minutes to one hour, but not specifically limited.

(5. Isoprene Polymer of the Present Invention)

The isoprene polymer of the present invention is characterized by its high cis-1,4 content in its micro structure. That is, the structural unit of the isoprene polymer can be classified into a cis-1,4 structural unit, a trans-1,4 structural unit, a 3,4 structural unit, or a 1,2 structural unit according to its coupling style. The isoprene polymer of the present invention means one having a high ratio of the cis-1,4 structural unit to all of the structural units. Specifically, the ratio of the cis-1,4 structural unit to the whole structural units is 90% or more, preferably 95% or more, more preferably 97% or more, still more preferably 99% or more. The ratio can be determined from $^1$H-NMR or $^{13}$C-NMR.

[Chem 12]

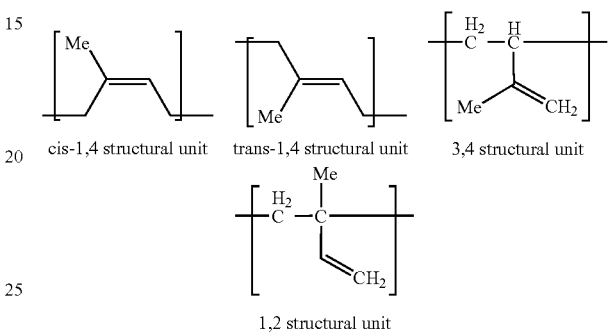

cis-1,4 structural unit   trans-1,4 structural unit   3,4 structural unit 1,2 structural unit The isoprene polymer of the present invention is characterized by not only the high ratio of the cis-1,4 structural unit as described above, but also characterized by small molecular weight distribution (Mw/Mn). The small molecular weight distribution means that Mw/Mn is 1.6 or less, preferably 1.5 or less, more preferably 1.3 or less, particularly preferably 1.2 or less.

The molecular weight distribution of the isoprene polymer of the present invention can be determined by the GPC method. For example, it can be determined by using a GPC-measuring apparatus (TOSOH HLC 8220 GPC, standard substance: polystyrene, eluate: tetrahydrofuran, measured at 40° C.).

A molecular weight of the isoprene polymer of the present invention is not specifically limited to, but a number average molecular weight Mn thereof is preferably $1 \times 10^4$ or more, more preferably $1 \times 10^5$ or more. The upper limit thereof is also not specifically limited but it may be $1 \times 10^7$ or less.

The number average molecular weight of the isoprene polymer of the present invention can be determined by the GPC method. Specifically, it can be determined by the same GPC method as one used in the measurement of the molecular weight distribution as described above.

The isoprene polymer of the present invention can be produced by polymerization of isoprene using the polymerization catalyst composition of the present invention as described above. For instance, isoprene may be polymerized by solution-polymerization with toluene or chlorobenzene as a solvent. The amount of the solvent to be used may be arbitrarily-selected.

The amounts of the complex and the ionic compound to be used in the polymerization are preferably at a mole ratio of about 1:1. In addition, the mole amount of the complex is preferably 0.00001 to 0.01 times higher than that of isoprene. The reaction temperature may be carried out at about room temperature and the reaction time period may be about several minutes to one hour, but not specifically limited.

In addition, a production example of an isoprene polymer is described in examples below.

(6. Butadiene Polymer of the Present Invention)

The butadiene polymer of the present invention is characterized by its high cis-1,4 content in its micro structure. The structural unit of the butadiene polymer can be classified into a cis-1,4 structural unit, a trans-1,4 structural unit, and a 1,2 structural unit according to its coupling style. The butadiene polymer of the present invention means one having a high ratio of the cis-1,4 structural unit to all of the structural units. Specifically, the ratio of the cis-1,4 structural unit to the whole structural units is 90% or more, preferably 95% or more, more preferably 98% or more, still more preferably 99% or more. The ratio can be determined from $^1$H-NMR or $^{13}$C-NMR.

The butadiene polymer of the present invention is characterized by not only the high ratio of the cis-1,4 structural unit as described above but also characterized by small molecular weight distribution (Mw/Mn). The small molecular weight distribution means that Mw/Mn is 1.6 or less, preferably 1.5 or less, more preferably 1.3 or less, particularly preferably 1.2 or less.

The molecular weight distribution of the butadiene polymer of the present invention can be determined by the GPC method. For example, it can be determined by using a GPC-measuring apparatus (TOSOH HLC 8220 GPC, standard substance: polystyrene, eluate: tetrahydrofuran, measured at 40° C.).

A molecular weight of the butadiene polymer of the present invention is not specifically limited to, but a number average molecular weight Mn thereof is preferably $1 \times 10^4$ or more, more preferably $1 \times 10^5$ or more. The upper limit thereof is also not specifically limited but it may be $1 \times 10^7$ or less.

The number average molecular weight of the butadiene polymer of the present invention can be determined by the GPC method. Specifically, it can be determined by the same GPC method as one used in the measurement of the molecular weight distribution as described above.

The butadiene polymer of the present invention can be produced by polymerization of butadiene by using the polymerization catalyst composition of the present invention as described above. For instance, butadiene may be polymerized by solution-polymerization with toluene or chlorobenzene as a solvent. The amount of the solvent to be used may be arbitrarily-selected.

The amounts of the complex and the ionic compound to be used in the polymerization are preferably at a mole ratio of about 1:1. In addition, the mole amount of the complex is preferably 0.00001 to 0.01 times higher than that of butadiene. The reaction may be carried out at about room temperature and the reaction time period may be about several minutes to one hour, but not specifically limited.

In addition, a production example of a butadiene polymer is described in examples given below.

(7. Isoprene-Styrene Copolymer of the Present Invention)

The isoprene-styrene copolymer of the present invention is characterized by its high cis-1,4 content of isoprene in its micro structure. Specifically, in all isoprene structural units within copolymer, the ratio of the cis-1,4 structural unit is 90% or more, preferably 95% or more, more preferably 97% or more. The ratio can be determined from $^1$H-NMR or $^{13}$C-NMR. In addition the content ratio of isoprene and styrene is not specifically limited, but the content of isoprene is preferably 5 to 95%, more preferably 10 to 90% in terms of weight ratio in the copolymer.

The isoprene-styrene copolymer of the present invention is characterized by not only the high ratio of the cis-1,4 structural unit as described above but also characterized by small molecular weight distribution (Mw/Mn). In general, the Mw/Mn is 2.0 or less but the small molecular weight distribution means that Mw/Mn is 1.6 or less, preferably 1.5 or less, more preferably 1.3 or less, particularly preferably 1.2 or less.

The molecular weight distribution of the isoprene-styrene copolymer of the present invention can be determined by the GPC method. For example, it can be determined using a GPC-measuring apparatus (TOSOH HLC 8220 GPC, standard substance: polystyrene, eluate: tetrahydrofuran, measured at 40° C.).

A molecular weight of the isoprene-styrene copolymer of the present invention is not specifically limited to, but a number average molecular weight Mn thereof is preferably $1 \times 10^4$ or more, more preferably $5 \times 10^4$ or more. The upper limit thereof is also not specifically limited but it may be $1 \times 10^7$ or less.

The number average molecular weight of the isoprene-styrene copolymer of the present invention can be determined by the GPC method. Specifically, it can be determined by the same GPC method as one used in the measurement of the molecular weight distribution as described above.

The isoprene-styrene copolymer of the present invention can be produced by polymerization of isoprene and styrene by using the polymerization catalyst composition of the present invention as described above. For instance, isoprene and styrene may be polymerized by solution-polymerization with toluene or chlorobenzene as a solvent. The amount of the solvent to be used may be arbitrarily-selected.

The amounts of the complex and the ionic compound to be used in the polymerization are preferably at a mole ratio of about 1:1. In addition, the mole amount of the complex is preferably 0.00001 to 0.01 times higher than that of isoprene. The reaction temperature may be carried out at about room temperature and the reaction time period may be about 1 to 48 hours, but not specifically limited.

In addition, a production example of an isoprene-styrene copolymer is described in examples below.

EXAMPLES

Hereinafter, the present invention is described in more detail with reference to examples and reference examples but the scope of the present invention will not be limited thereto.

(Tridentate Ligand Precursor: Synthesis of Bis(2-diphenylphosphinophenyl)amine)

Under argon atmosphere, a toluene solution prepared by adding toluene (90 ml) to 2-fluoroaniline (120 mmol), 1-bromo-2-fluorobenene (100 mmol), paradium acetate (0.5 mmol), BINAP (0.75 mmol), and KOBu$^t$ (140 mmol) was refluxed for one day. After cooling to room temperature, water (200 ml) was added to the mixture and an organic compound was then extracted by toluene. A low boiling point material was distilled off from a resulting organic layer under reduced pressure and obtaining bis(2-fluorophenyl)amine as a dark purple liquid (a crude yield of 100%).

THF was removed from a commercially-available KPPh$_2$ in THF solution (0.5 M, 100 ml), and then a solution in which the resulting bis(2-fluorophenyl)amine (50 g, 24.4 mmol) was added and dissolved in 1,4-dioxane (40 ml) was added thereto. The resulting solution was refluxed for two days. After cooling to room temperature, the solvent was distilled off and the residue thus obtained was added with water and dichloromethane to separate an organic layer, followed by extracting the organic layer from a water layer with dichloromethane. A low boiling point material was distilled off from the organic layer under reduced pressure and then dried under reduced pressure. Ethanol was added to the residual oil and a precipitated white solid was then obtained by filtration. The white solid thus obtained was washed with ethanol and recrystallized from dichloromethane/ethanol, thereby obtaining bis(2-diphenylphosphinophenyl)amine as a transparent crystal.

[Chem 13]

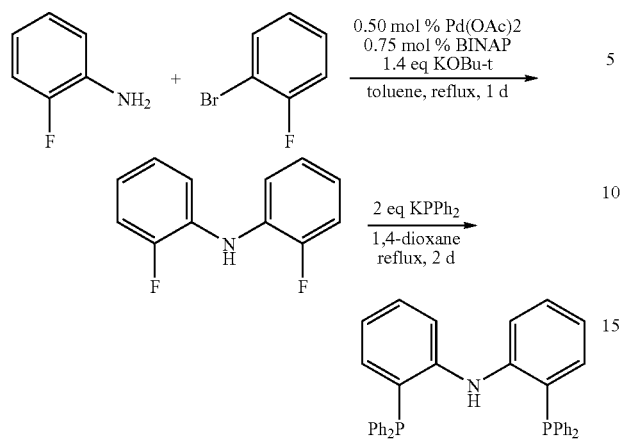

Example 1

Synthesis of Complex

Under nitrogen atmosphere, YCl$_3$ (1.96 g, 10.0 mmol) was suspended in THF (20 ml) and then add by dripping down with Li(CH$_2$SiMe$_3$) (2.86 g, 30 mmol) in THF solution (20 ml) for 1 hour at room temperature. After dripping down, THF was removed from the resulting solution under reduced pressure. Hexane was added to the residue and an insoluble material was then removed by filtration. The filtrate was concentrated and the concentrated product was then cooled to −20° C. After a separated oily product in the bottom of a vessel was removed, a low boiling point material was completely removed under reduced pressure, thereby obtaining a tris (trimethylsilylmethyl) yttrium complex [Y(CH$_2$SiMe$_3$)$_3$(thf)$_2$]

Bis (2-diphenylphosphinophenyl)amine (88 mg, 0.20 mmol) in THF solution (1.0 ml) was added by dripping down to the above obtained complex [Y(CH$_2$SiMe$_3$)$_3$(thf)$_2$] (100 mg, 0.20 mmol) in THF solution (5.0 ml) at room temperature. After dripping down, the color of the solution varied from light yellow to strong yellow immediately. The low boiling point material was removed from the resulting solution under reduced pressure and then dried under reduced pressure, thereby obtaining [Y(CH$_2$SiMe$_3$)$_2$(PNP) (thf)] as a crude product (almost quantitative). The resulting crude product was recrystallized from toluene/hexane, thereby isolating [Y(CH$_2$SiMe$_3$)$_2$(PNP)(thf)] as a yellow crystal. Here, PNP represents bis(2-diphenylphosphinophenyl) amido, which is a tridentate ligand.

$^1$H-NMR (C$_6$D$_6$, δ/ppm): 7.48 (m, 8H, aromatic), 7.1-6.9 (m, 18H, aromatic), 6.56 (t, 2H, aromatic), 3.59 (br, 4H, THF), 1.16 (br, 4H, THF), 0.28 (s, 18H, 6Me), −0.01 (s, 4H, 2CH$_2$)

$^{31}$P-NMR(C$_6$D$_6$, δ/ppm): −10.8 (d, J$_{YP}$=39 Hz)

[Chem 14]

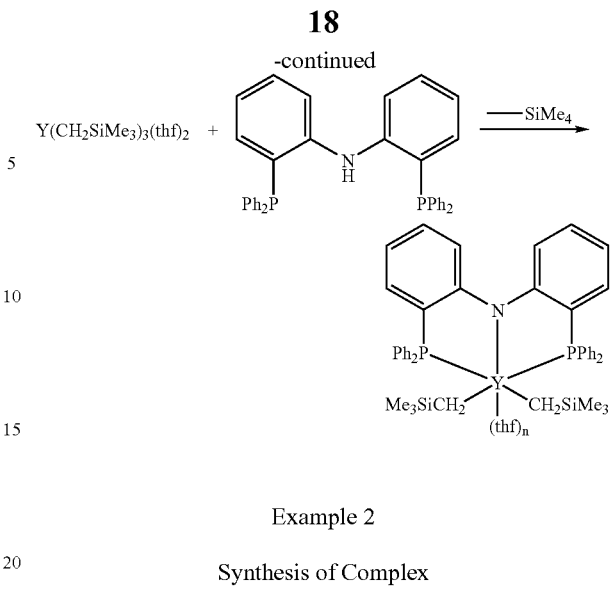

Example 2

Synthesis of Complex

[Sc(CH$_2$SiMe$_3$)$_3$ (thf)$_2$] was obtained by the same way as that of Example 1 except that ScCl$_3$ was used instead of YCl$_3$. Furthermore, [Sc(CH$_2$SiMe$_3$)$_2$(PNP)] was isolated (THF molecule was uncoordinated on the resulting Sc complex).

$^1$H-NMR (C$_6$D$_6$, δ/ppm): 7.60 (m, 8H, aromatic), 7.1-6.9 (m, 18H, aromatic), 6.55 (t, 2H, aromatic), 0.12 (s, 18H, 6Me), −0.16 (s, 4H, 2CH$_2$)

$^{31}$P-NMR (C$_6$D$_6$, δ/ppm): −8.3 (s)

Example 3

Synthesis of Complex

[Lu(CH$_2$SiMe$_3$)$_3$(thf)$_2$] was obtained by the same way as that of Example 1 except that LuCl$_3$ was used instead of YCl$_3$. Furthermore, [Lu(CH$_2$SiMe$_3$)$_3$(thf)$_2$] was obtained and [Lu (CH$_2$SiMe$_3$)$_2$(PNP) (thf)] was isolated.

$^1$H-NMR (C$_6$D$_6$, δ/ppm): 7.54 (m, 8H, aromatic), 7.1-6.9 (m, 18H, aromatic), 6.54 (t, 2H, aromatic), 3.62 (br, 4H, THF), 1.21 (br, 4H, THF), 0.22 (s, 18H, 6Me), −0.12 (s, 4H, 2CH$_2$)

$^{31}$P-NMR (C$_6$D$_6$, δ/ppm): 0.5 (s)

The complex [Lu (CH$_2$SiMe$_3$)$_2$(PNP) (thf)] was recrystallized from toluene to obtain an yellow single-crystal and the structure thereof was then determined by X-ray crystal structure analysis. The measurement was carried out at −100° C. and obtaining with a direct method, followed by refining with respect to the square of the structural factor F (F$^2$). R and wR2 factors that indicate the degree of correspondence between the structural model and the actual crystal structure are 0.0285 and 0.0709, respectively. The GOF value, which indicates the degree of adaptation of the structural model, was 0.999. A crystal solvent containing 0.5 toluene molecule per complex molecule and the molecular formula thereof was C$_{51.5}$H$_{62}$LuNOP$_2$Si$_2$ with a molecular weight of 1004.11. A crystalline system was a triclinic system with a space group of P-1, where two complex molecules resided in one unit lattice. Lattice parameters included lengths of three sides of a=12.314 (1), b=13.805 (2), and c=16.555 (2) Å, three angles of α=88.689 (2), β=80.048 (1), and γ=65.261 (1), a volume of 2513.7 (5) Å$^3$, a density (calculated value) of 1.327 g cm$^{-3}$, and a linear absorption coefficient μ (Mo—K α) of 21.10 cm$^{-1}$. FIG. 3 shows an ORTEP diagram. However, hydrogen atoms and a crystalline solvent are omitted.

Example 4

Production of Isoprene Polymer

In a glass reaction container (100 ml) in a globe box under nitrogen atmosphere, [Y(CH$_2$SiMe$_3$)$_2$(PNP)(thf) (0.22 g, 25 µmol) of chlorobenzene solution (5 ml) and isoprene (1.022 g, 15 mmol) were added, then chlorobenzene solution (5 ml) of [PhMe$_2$NH][B(C$_6$F$_5$)$_4$] (0.020 g, 25 µmol) was added. The mixture was reacted for 20 minutes at room temperature and then added with methanol to terminate the polymerization. The reaction solution was poured into a methanol solution containing a small amount of hydrochloric acid and butyl hydroxytoluene (stabilizer). The precipitated polymer product was filtrated and then washed with methanol and dried for 48 hours at 50° C., thereby obtaining 1.02 g of polymer (Yield: 100%).

Example 5

Production of Isoprene Polymer

A polymer was obtained by the same way as that of Example 4 except that the reaction time was set to 10 minutes (Yield: 40%).

Example 6

Production of Isoprene Polymer

A polymer was obtained by the same way as that of Example 4 except that the reaction time was set to 15 minutes (Yield: 90%).

Example 7

Production of Isoprene Polymer

A polymer was obtained by the same way as that of Example 4 except that the reaction temperature was set to 0° C. and the reaction time was set to 3 hours (Yield: 100%).

Example 8

Production of Isoprene Polymer

A polymer was obtained by the same way as that of Example 4 except that the reaction temperature was set to 50° C. and the reaction time was set to 10 minutes (Yield: 100%).

Example 9

Production of Isoprene Polymer

A polymer was obtained by the same way as that of Example 4 except that a reaction was carried out at room temperature for 30 minutes and isoprene (1.022 g, 15 mmol) are additionally provided for an additional reaction at room temperature for 30 minutes (Yield: 100%).

Example 10

Production of Isoprene Polymer

A polymer was obtained by the same way as that of Example 4 except that [Ph$_3$C][B(C$_6$F$_5$)$_4$] was used instead of [PhMe$_2$NH][B(C$_6$F$_5$)$_4$] and the reaction time was set to 1 hour (Yield: 79%).

Example 11

Production of Isoprene Polymer

A polymer was obtained by the same way as that of Example 10 except that toluene was used instead of chlorobenzene (Yield: 51%).

Comparative Example 1

A small amount of polymer was obtained by the same way as that of Example 4 except that B(C$_6$F$_5$)$_3$ was used instead of [PhMe$_2$NH][B(C$_6$F$_5$)$_4$] and the reaction time was set to 1 hour.

Comparative Example 2

The reaction was carried out by the same way as that of Example 4 except that [PhMe$_2$NH][B(C$_6$F$_5$)$_4$] was not used and the reaction time was set to 1 hour. However, a polymer could not be obtained.

The number average molecular weights, molecular weight distributions, micro structures, and glass transition temperatures of the polymers obtained in Examples 4 to 11 were described in Table 1, respectively. The number average molecular weight and the molecular weight distribution were determined using the GPC as described above (standard substance: polystyrene). The micro structure was determined using $^1$H-NMR and $^{13}$C-NMR. The glass transition temperature was measured using DSC.

TABLE 1

| Examples | Catalyst composition Complex | Catalyst activating agent | Temperature (° C.) | Time (Minutes) | Yield (%) | Number average molecular weight Mn (×10$^5$) | Molecular weight distribution Mw/Mn | Micro structure (%) Cis-1,4 | 3,4 | Glass transition temperature Tg (° C.) |
|---|---|---|---|---|---|---|---|---|---|---|
| Example 4 | Y | [PhMe$_2$NH][B(C$_6$F$_5$)$_4$] | Room temperature | 20 | 100 | 1.2 | 1.07 | 99.3 | <0.7 | −69° C. |
| Example 5 | Y | [PhMe$_2$NH][B(C$_6$F$_5$)$_4$] | Room temperature | 10 | 40 | 0.5 | 1.05 | 99.3 | <0.7 | −69° C. |
| Example 6 | Y | [PhMe$_2$NH][B(C$_6$F$_5$)$_4$] | Room temperature | 15 | 90 | 1.0 | 1.05 | 99.3 | <0.7 | −69° C. |
| Example 7 | Y | [PhMe$_2$NH][B(C$_6$F$_5$)$_4$] | 0 | 180 | 100 | 1.3 | 1.06 | 99.6 | <0.4 | −69° C. |
| Example 8 | Y | [PhMe$_2$NH][B(C$_6$F$_5$)$_4$] | 50 | 10 | 100 | 1.3 | 1.05 | 99.3 | <0.7 | −68° C. |
| Example 9 | Y | [PhMe$_2$NH][B(C$_6$F$_5$)$_4$] | Room temperature | Total 60 | 100 | 2.3 | 1.08 | 99.3 | <0.7 | −69° C. |

TABLE 1-continued

Table 1

| Examples | Catalyst composition Complex | Catalyst activating agent | Temperature (° C.) | Time (Minutes) | Yield (%) | Number average molecular weight Mn (×10$^5$) | Molecular weight distribution Mw/Mn | Micro structure (%) Cis-1,4 | 3,4 | Glass transition temperature Tg (° C.) |
|---|---|---|---|---|---|---|---|---|---|---|
| Example 10 | Y | [Ph$_3$C][B(C$_6$F$_5$)$_4$] | Room temperature | 60 | 79 | 3.2 | 1.11 | 99.4 | <0.6 | −69° C. |
| Example 11 | Y | [Ph$_3$C][B(C$_6$F$_5$)$_4$] | Room temperature | 60 | 51 | 0.6 | 1.05 | 98.9 | <1.1 | −69° C. |
| Comparative example 1 | Y | B(C$_6$F$_5$)$_3$ | Room temperature | 60 | trace | n.d. | n.d. | n.d. | n.d. | n.d. |
| Comparative example 2 | Y | None | Room temperature | 60 | 0 | — | — | — | — | — |

In Table 1, Y shown in the column of "Complex" represents [Y(CH$_2$SiMe$_3$)$_2$(PNP)(thf)].

As is evident from Table 1, isoprene can be polymerized using the complex of the present invention. In addition, it is found that the isoprene polymer thus obtained has a cis-1,4 content of about 100% while a molecular-weight distribution being extremely sharp.

Example 12

Synthesis of Complex

Under nitrogen atmosphere, YCl$_3$ (1.96 g, 10.0 mmol) was suspended in THF (20 ml) and Li(CH$_2$C$_6$H$_4$NMe$_2$-o) (4.24 g, 30 mmol) in THF solution (20 ml) was then added dropwise to the suspension for 15 minutes at room temperature. After completing the dropping, the mixture was stirred for 30 minutes and THF was then removed from the resulting solution under reduced pressure. Toluene was added to the residue and an insoluble material was then removed through filtration. The filtrate was concentrated and the concentrated product was then cooled to −20° C., thereby obtaining tris(o-N,N-dimethylaminobenzyl) yttrium complex [Y(CH$_2$C$_6$H$_4$NMe$_2$-o)$_3$].

Bis(2-diphenylphosphinophenyl)amine (1.73 g, 3.21 mmol) in toluene solution (20 ml) was added dropwise to the complex Y(CH$_2$C$_6$H$_4$NMe$_2$-o)$_3$(1.58 g, 3.21 mmol) in toluene solution (5.0 ml) obtained as described above at room temperature for 20 minutes and stirred for 24 hours. After the dropping, the color of the solution was turned from light yellow to strong yellow. A low boiling point material was removed from the resulting solution under reduced pressure and the residue was then washed twice with cooled 5 ml of n-hexane. Subsequently, it was dried under reduced pressure, thereby obtaining [Y(CH$_2$C$_6$H$_4$NMe$_2$-o)$_2$(PNP)]. The resulting product was yellow powder (Yield: 2.439 g, 85%).

$^1$H-NMR (C$_6$D$_6$, δ/ppm): 7.91 (m, 8H, aromatic), 7.06 (m, 2H, aromatic), 7.01 (m, 12H, aromatic), 6.85 (t, 4H, aromatic), 6.73 (d, 2H, aromatic), 6.67 (m, 4H, aromatic), 6.61 (m, 2H, aromatic), 6.53 (t, 2H, aromatic), 2.46 (s, 12H, 4Me), 1.99 (s, 4H, 2CH$_2$)

$^{31}$P-NMR (C$_6$D$_6$, δ/ppm): −8.46 (d, J$_{YP}$=35 Hz)

The complex [Y(CH$_2$C$_6$H$_4$NMe$_2$)$_2$ (PNP)] was recrystallized from toluene to obtain an yellow single-crystal and the structure thereof was then determined by X-ray crystal structure analysis. The measurement was carried out at −100° C. and obtaining with a direct method, followed by refining with respect to the square of the structural factor F (F$^2$). R and wR2 factors that indicate the degree of correspondence between the structural model and the actual crystal structure are 0.0587 and 0.1553, respectively. The GOF value, which indicates the degree of adaptation of the structural model, was 1.083. A crystal solvent containing three toluene molecules per complex and the molecular formula thereof was C$_{75}$H$_{76}$N$_3$P$_2$Y with a molecular weight of 1182.25. A crystalline system was a triclinic system with a space group of P-1, where two complex molecules resided in one unit lattice. Lattice parameters include lengths of three sides of a=14.314 (2), b=15.038 (2), and c=16.107 (2) Å, three angles of α=69.089 (2), β=66.875 (2), and γ=84.181 (2)°, a volume of 2975.4 (6) Å$^3$, a density (calculated value) of 1.320 g cm$^{-3}$, and a linear absorption coefficient μ (Mo—K α) of 10.82 cm$^{-1}$. FIG. 9 shows an ORTEP diagram, but hydrogen atoms and a crystalline solvent are omitted.

[Chem 15]

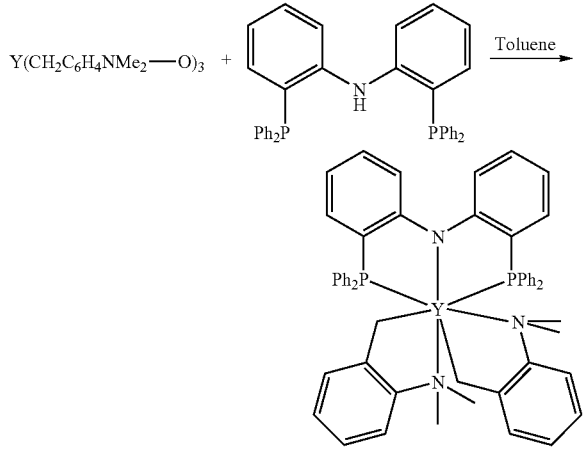

Example 13

Synthesis of Complex

[Sc(CH$_2$C$_6$H$_4$NMe$_2$-o)$_3$] was obtained by the same way as that of Example 12 except that ScCl$_3$ was used instead of YCl$_3$. Furthermore, [Sc(CH$_2$C$_6$H$_4$NMe$_2$-o)$_2$(PNP)] was isolated.

$^1$H-NMR(C$_6$D$_6$, δ/ppm): 7.42 (m, 8H, aromatic), 7.11 (t, 2H, aromatic), 7.02 (m, 12H, aromatic), 6.90 (m, 2H, aromatic), 6.85-6.75 (m, 8H, aromatic), 6.63-6.55 (m, 4H, aromatic), 2.50 (s, 12H, 4Me), 2.33 (s, 4H, 2CH$_2$)

$^{31}$P-NMR (C$_6$D$_6$, δ/ppm): −10.2 (s)

Example 14

Synthesis of Complex

[Lu(CH$_2$C$_6$H$_4$NMe$_2$-o)$_3$] was obtained by the same way as that of Example 12 except that LuCl$_3$ was used instead of YCl$_3$. Furthermore, [Lu(CH$_2$C$_6$H$_4$NMe$_2$-o) 2 (PNP)] was isolated.

$^1$H-NMR (C$_6$D$_6$, δ/ppm): 7.30 (m, 8H, aromatic), 7.05 (t, 2H, aromatic), 7.01 (m, 12H, aromatic), 6.86 (m, 4H, aromatic), 6.78-6.68 (m, 6H, aromatic), 6.59 (m, 2H, aromatic), 6.54 (t, 2H, aromatic), 2.48 (s, 12H, 4Me), 1.96 (s, 4H, 2CH$_2$)

$^{31}$P-NMR (C$_6$D$_6$, δ/ppm): −3.82 (s)

Example 15

Synthesis of Complex

[La(CH$_2$C$_6$H$_4$NMe$_2$-o)$_3$] was obtained by the same way as that of Example 12 except that La(OSO$_2$CF$_3$)$_3$ was used instead of YCl$_3$. Furthermore, [La(CH$_2$C$_6$H$_4$NMe$_2$-o)$_2$ (PNP)] was isolated.

$^1$H-NMR (C$_6$D$_6$, δ/ppm): 7.42 (m, 8H, aromatic), 7.0-7.15 (m, 14H, aromatic), 6.88 (m, 4H, aromatic), 6.81 (m, 2H, aromatic), 6.65 (m, 2H, aromatic), 6.54 (m, 6H, aromatic), 2.20 (s, 12H, 4Me), 2.15 (s, 4H, 2CH$_2$)

$^{31}$P-NMR (C$_6$D$_6$, δ/ppm): 0.87 (s)

Example 16

Production of Isoprene Polymer

In a globe box, a magnetic stirring bar was placed in a flask (100 ml) and then added with isoprene (1.022 g, 15.0 mmol), [Y (CH$_2$C$_6$H$_4$NMe$_2$-o) 2 (PNP)] (0.023 g, 25 µmol) in chlorobenzene solution (8 ml). Subsequently, under high-speed stirring, [PhMe$_2$NH] [B(C$_6$F$_5$)$_4$] (0.020 g, 25 µmol) in chlorobenzene solution (2 ml) was added. The reaction proceeded while stirring at room temperature for 5 minutes and the polymerization was then terminated by the addition of methanol. The reaction solution was poured into 200 ml of a methanol solution containing small amounts of hydrochloric acid and butylhydroxyl toluene (stabilizer). The precipitated polymer product was separated by decantation, washed with methanol, and dried at 60° C., thereby obtaining 1.021 g of polymer (Yield: 100%).

Example 17

Production of Isoprene Polymer

A polymer was obtained by the same way as that of Example 16 except that 12.5 µmol of [Y(CH$_2$C$_6$H$_4$NMe$_2$-o)$_2$(PNP)] and 12.5 µmol of [PhMe$_2$NH][B(C$_6$F$_5$)$_4$] were added (Yield: 100%).

Example 18

Production of Isoprene Polymer

A polymer was obtained by the same way as that of Example 16 except: isoprene (2.044 g, 30.0 mmol) and [Y(CH$_2$C$_6$H$_4$NMe$_2$-o)$_2$(PNP)] (12.5 µmol) in chlorobenzene solution (16 ml) were added and then stirred at high speed while adding [PhMe$_2$NH] [B(C$_6$F$_5$)$_4$] (12.5 µmol) in chlorobenzene solution (4 ml); and a reaction hour was set to 2 minutes (Yield: 100%).

Example 19

Production of Isoprene Polymer

A polymer was obtained by the same way as that of Example 18 except that a toluene solution was used instead of the chlorobenzene solution (Yield: 73%).

Example 20

Production of Isoprene Polymer

A polymer was obtained by the same way as that of Example 16 except that [Sc(CH$_2$C$_6$H$_4$NMe$_2$-o)$_2$ (PNP)] was used instead of [Y(CH$_2$C$_6$H$_4$NMe$_2$-o)$_2$(PNP)] (Yield: 100%).

Example 21

Production of Isoprene Polymer

A polymer was obtained by the same way as that of Example 19 except that [Sc(CH$_2$C$_6$H$_4$NMe$_2$-o)$_2$(PNP)] was used instead of [Y(CH$_2$C$_6$H$_4$NMe$_2$-o)$_2$(PNP)] (Yield: 9%).

Example 22

Production of Isoprene Polymer

A polymer was obtained by the same way as that of Example 16 except that [Lu(CH$_2$C$_6$H$_4$NMe$_2$-o)$_2$(PNP)] was used instead of [Y(CH$_2$C$_6$H$_4$NMe$_2$-o)$_2$(PNP)] (Yield: 100%).

Example 23

Production of Isoprene Polymer

A polymer was obtained by the same way as that of Example 19 except that [Lu (CH$_2$C$_6$H$_4$NMe$_2$-o)$_2$(PNP)] was used instead of [Y(CH$_2$C$_6$H$_4$NMe$_2$-o)$_2$(PNP)] (Yield: 55%).

Example 24

Production of Isoprene Polymer

A polymer was obtained by the same way as that of Example 16 except that [La(CH$_2$C$_6$H$_4$NMe$_2$-o)$_2$(PNP)] was used instead of [Y(CH$_2$C$_6$H$_4$NMe$_2$-o)$_2$(PNP)] (Yield: 100%).

Example 25

Production of Isoprene Polymer

A polymer was obtained by the same way as that of Example 17 except that [La(CH$_2$C$_6$H$_4$NMe$_2$-o)$_2$(PNP)] was used instead of [Y(CH$_2$C$_6$H$_4$NMe$_2$-o)$_2$(PNP)] (Yield: 100%).

Example 26

Production of Isoprene Polymer

A polymer was obtained by the same way as that of Example 18 except that [La(CH$_2$C$_6$H$_4$NMe$_2$-o)$_2$(PNP)] was used instead of [Y(CH$_2$C$_6$H$_4$NMe$_2$-o)$_2$(PNP)] and a reaction time was set to 5 minutes (Yield: 100%).

The number average molecular weights, molecular weight distributions, micro structures, and glass transition temperatures of the polymers obtained in Examples 16 to 26 were described in Table 2, respectively. The number average molecular weight and the molecular weight distribution were determined using the GPC as described above (standard substance: polystyrene). The micro structure was determined using $^1$H-NMR and $^{13}$C-NMR. The glass transition temperature was measured using DSC.

TABLE 2

Table 2

| | Complex | [monomer]/[Catalyst] | Time (Minutes) | Yield (%) | Number average molecular weight Mn (×10$^5$) | Molecular weight distribution Mw/Mn | Micro structure (%) Cis-1,4 | 3,4 | Glass transition temperature Tg (° C.) |
|---|---|---|---|---|---|---|---|---|---|
| Example 16 | Y | 600 | 5 | 100 | 1.2 | 1.28 | 98 | 2 | −65 |
| Example 17 | Y | 1200 | 5 | 100 | 2.2 | 1.42 | 98 | 2 | −65 |
| Example 18 | Y | 2400 | 2 | 100 | 4.1 | 1.26 | 98 | 2 | −65 |
| Example 19 | Y | 2400 | 2 | 73 | 2.3 | 1.11 | 98 | 2 | −66 |
| Example 20 | Sc | 600 | 5 | 100 | 1.7 | 1.36 | 98 | 2 | −65 |
| Example 21 | Sc | 2400 | 2 | 9 | 0.9 | 1.26 | 98 | 2 | −66 |
| Example 22 | Lu | 600 | 5 | 100 | 1.7 | 1.39 | 98 | 2 | −65 |
| Example 23 | Lu | 2400 | 2 | 55 | 2.3 | 1.22 | 98 | 2 | −66 |
| Example 24 | La | 600 | 5 | 100 | 0.9 | 1.07 | 98 | 2 | −65 |
| Example 25 | La | 1200 | 5 | 100 | 1.7 | 1.09 | 98 | 2 | −65 |
| Example 26 | La | 2400 | 5 | 100 | 5.0 | 1.07 | 98 | 2 | −65 |

In Table 2, in the column of "Complex", Y represents [Y(CH$_2$C$_6$H$_4$NMe$_2$-o)$_2$(PNP)], Sc represents [Sc(CH$_2$C$_6$H$_4$NMe$_2$-o)$_2$(PNP)], Lu represents [Lu(CH$_2$C$_6$H$_4$NMe$_2$-o)$_2$(PNP)], and La represents [La(CH$_2$C$_6$H$_4$NMe$_2$-o)$_2$(PNP)].

As is evident from Table 2, isoprene can be polymerized using the complex of the present invention. In addition, it is found that the isoprene polymer thus obtained has a cis-1,4 content of about 100% while a molecular-weight distribution being extremely sharp.

Example 27

Production of Butadiene Polymer

In a globe box, 1-M triisobutyl aluminum (Al$^i$Bu$_3$) in toluene solution (0.250 ml, 250 μmol) and 11 ml of toluene were placed in a pressure-resistance glass container and the reaction container was then sealed off, followed by taking out of the globe box. Subsequently, butadiene (0.810 g, 15.0 mmol) was added to the solution at −10° C. and the reaction container was then placed in a water bath at 25° C., followed by addition of [Y(CH$_2$SiMe$_3$)$_2$(PNP)(thf)] (22 mg, 25 μmol) in toluene solution (4 ml). The polymerization mixture was stirred at high speed for 10 minutes to react and then added with a small amount of acidic methanol to terminate the polymerization reaction. The reaction solution was poured in to a methanol solution containing small amounts of hydrochloric acid and butylhydroxyl toluene. The precipitated polymer product was filtrated, washed with methanol, and dried at 60° C., there by obtaining 0.170 g of polymer (Yield: 21%).

Example 28

Production of Butadiene Polymer

A polymer was obtained by the same way as that of Example 27 except that Al$^i$Bu$_3$ was set to 1.250 ml and [Y(CH$_2$SiMe$_3$)$_2$(PNP)(thf)] was added together with [Ph$_3$C][B(C$_6$F$_5$)$_4$] (23 mg, 25 μmol) (Yield: 100%).

Example 29

Production of Butadiene Polymer

A polymer was obtained by the same way as that of Example 28 except that Al$^i$Bu$_3$ was set to 0.250 ml (Yield: 100%).

Example 30

Production of Butadiene Polymer

A polymer was obtained by the same way as that of Example 28 except that Al$^i$Bu$_3$ was set to 0.125 ml (Yield: 100%).

Example 31

Production of Butadiene Polymer

A polymer was obtained by the same way as that of Example 30 except that butadiene was set to 0.665 g, 6 ml of chlorobenzene was used instead of 11 ml of toluene, and [Y(CH$_2$SiMe$_3$)$_2$(PNP)(thf)] and [Ph$_3$C][B(C$_6$F$_5$)$_4$] in 4 ml of a chlorobenzene solution was used instead of those in 4 ml of toluene solution (Yield: 100%).

Example 32

Production of Butadiene Polymer 0.324 g of a polymer was obtained by the same way as that of Example 30 except that a reaction temperature was set to −10° C. (Yield: 40%).

Example 33

Production of Butadiene Polymer 0.810 g of a polymer was obtained by the same way as that of Example 27 except that $Al^iBu_3$ was not added, and $[Y(CH_2SiMe_3)_2(PNP)(thf)]$ in 12 ml of toluene solution and $[Ph_3C][B(C_6F_5)_4]$ in 3 ml of toluene solution were added to the reaction solution (Yield: 100%).

The number average molecular weights, molecular weight distributions, micro structures, and glass transition temperatures of the polymers obtained in Examples 27 to 33 were described in Table 3, respectively. The number average molecular weight and the molecular weight distribution were determined using the GPC as described above (standard substance: polystyrene). The micro structure was determined using $^1$H-NMR and $^{13}$C-NMR. The glass transition temperature was measured using DSC.

mmol) in chlorobenzene solution (2 ml) and stirring at high-speed. There action proceeded while stirring for 5 hours at room temperature and was then terminated by the addition of methanol. The reaction solution was poured into 200 ml of a methanol solution containing small amounts of hydrochloric acid and butylhydroxyl toluene. The precipitated polymer product was separated by decantation, washed with methanol, and dried at 60° C., thereby obtaining 1.230 g of copolymer.

Example 35

Production of Isoprene-Styrene Copolymer 1.186 g of a copolymer was obtained by the same way as that of Example 34 except that styrene was set to 1.562 g and a reaction time was set to 15 hours.

Example 36

Production of Isoprene Polymer 1.022 g of a polymer was obtained by the same way as that of Example 34 except that styrene was not added and a reaction time was set to 0.5 hour.

TABLE 3

Table 3

| | Complex | $Al^iBu_3$ (μmol) | $[Ph_3C][B(C_6F_5)_4]$ (μmol) | Temperature (° C.) | Time (Minutes) | Yield (%) | Number average molecular weight Mn (×10$^5$) | Molecular weight distribution Mw/Mn | Micro structure (%) | | | Tg (° C.) | Tc (° C.) | Tm (° C.) |
|---|---|---|---|---|---|---|---|---|---|---|---|---|---|---|
| | | | | | | | | | Cis | Trans-1,4 | 1,2 | | | |
| Example 27 | Y | 250 | — | 25 | 10 | 21 | 0.57 | 1.61 | 99 | 0.75 | 0.25 | −103 | −39 | −7 |
| Example 28 | Y | 1250 | 25 | 25 | 10 | 100 | 0.61 | 1.63 | 99 | 0.85 | 0.15 | −105 | −34 | −9 |
| Example 29 | Y | 250 | 25 | 25 | 10 | 100 | 1.30 | 1.09 | 99 | 0.85 | 0.15 | −107 | −38 | −8 |
| Example 30 | Y | 125 | 25 | 25 | 10 | 100 | 1.46 | 1.09 | 99 | 0.85 | 0.15 | −107 | −48 | −6 |
| Example 31 | Y | 125 | 25 | 25 | 10 | 100 | 0.39 | 1.51 | 99 | 0.85 | 0.15 | −106 | −49 | −9 |
| Example 32 | Y | 125 | 25 | −10 | 10 | 40 | 1.80 | 1.47 | 99.5 | 0.40 | 0.10 | −106 | −41 | −4 |
| Example 33 | Y | — | 25 | 25 | 10 | 100 | 1.70 | 1.10 | 99 | 0.80 | 0.20 | −105 | −42 | −8 |

In Table 3, Y shown in the column of "Complex" represents $[Y(CH_2SiMe_3)_2(PNP)(thf)]$.

As is evident from Table 3, butadiene can be polymerized using the complex of the present invention. In addition, it is found that the butadiene polymer thus obtained has a cis-1,4 content of about 100% while a molecular weight distribution being extremely sharp.

Example 34

Production of Isoprene-Styrene Copolymer

In a globe box, a magnetic stirring bar was placed in a flask (100 ml) and then added with isoprene (1.022 g, 15.0 mmol), styrene (3.124 g, 30.0 mmol), and $[Sc(CH_2SiMe_3)_2 (PNP)]$ (0.019 g, 0.025 mmol) in chlorobenzene solution (8 ml), followed by the addition of $[Ph_3C][B(C_6F_5)_4]$ (0.023 g, 0.025

Example 37

Production of Styrene Polymer 0.39 g of a polymer was obtained by the same way as that of Example 35 except that isoprene was not added and a reaction time was set to 1 hour.

The number average molecular weights, molecular weight distributions, micro structures, and glass transition temperatures of the polymers obtained in Examples 34 to 37 were described in Table 4, respectively. The number average molecular weight and the molecular weight distribution were determined using the GPC as described above (standard substance: polystyrene). The micro structure was determined using $^1$H-NMR and $^{13}$C-NMR. The glass transition temperature was measured using DSC.

TABLE 4

| | | Monomer | | | | Number average molecular | Molecular weight | Micro structure (%) | | Content (wt %) | | Tg |
| | | Styrene | Isoprene | Time | Yield | weight | distribution | Cis-1,4- | 3,4- | | | |
| | Complex | (g) | (g) | (Hours) | (g) | Mn (×10$^5$) | Mw/Mn | isoprene | isoprene | Styrene | Isoprene | Styrene | (° C.) |
|---|---|---|---|---|---|---|---|---|---|---|---|---|---|
| Example 34 | Sc | 3.124 | 1.022 | 5 | 1.230 | 0.81 | 1.55 | 85 | 3 | 12 | 83 | 17 | −59 |
| Example 35 | Sc | 1.562 | 1.022 | 15 | 1.186 | 0.80 | 1.17 | 89 | 4 | 7 | 86 | 14 | −59 |
| Example 36 | Sc | 0 | 1.022 | 0.5 | 1.022 | 0.69 | 1.08 | 97 | 3 | 0 | 100 | 0 | −66 |
| Example 37 | Sc | 1.562 | 0 | 1 | 0.39 | 0.19 | 1.04 | 0 | 0 | 100 | 0 | 100 | 97 |

In Table 4, Sc shown in the column of "Complex" represents [Sc(CH$_2$C$_6$SiMe$_3$)$_2$(PNP)(thf)].

As shown in Table 4, the complex of the present invention can be used in polymerization of isoprene with styrene. In addition, in the isoprene-styrene copolymer thus obtained, the cis-1,4 content of isoprene was high as 95% or more with respect to all of the isoprenes in the copolymer while a molecular weight distribution being extremely sharp.

INDUSTRIAL APPLICABILITY

A novel polymerization catalyst is provided by a complex of the present invention, and a process for producing a polymer using the polymerization catalyst are further provided.

In addition, by using the polymerization catalyst provided by the complex of the present invention, a high-cis-1,4-isoprene polymer, a high-cis-1,4-butadiene polymer, a high-cis-1,4-isoprene-styrene copolymer, a high-cis-1,4-butadiene-styrene copolymer, a high-cis-1,4-butadine-high-cis-1,4-isoprene copolymer, and a high-cis-1,4-butadiene-high-cis-1,4-isoprene-styrene copolymer, each of which has a sharp molecular distribution, are provided. The polymer has a high abrasion resistance and is a high-strength rubber, so it can be applied to a wide range of applications (e.g., tires, rubber belts, adhesive agents, and medical supplies).

The invention claimed is:

1. A complex comprising a mono-anionic tridentate ligand, represented by the following general formula (I):

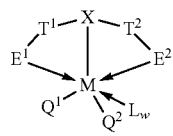

(I)

wherein in the general formula (I),
M represents scandium Sc, yttrium Y, or lanthanoid;
E$^1$-T$^1$-X-T$^2$-E$^2$ represents a mono-anionic tridentate ligand;
X represents an anionic electron-donating group containing a ligand atom selected from Group-15 atoms;
E$^1$ and E$^2$ each represent independently a neutral electron-donating group containing a ligand atom selected from one of Group-15 atoms and Group-16 atoms;
T$^1$ and T$^2$ are cross-linking groups that cross-link X with E$^1$ and E$^2$, and each represent independently an arylene group which may have a substituent on an aryl ring;
Q$^1$ and Q$^2$ each represent independently a monoanionic ligand;

L represents a neutral Lewis base; and w represents an integral of 0 to 3.

2. The complex according to claim 1, wherein each of the T$^1$ and T$^2$ in the general formula (I) is a phenylene group which may have a substituent on a phenyl ring.

3. The complex according to claims 1 or 2, wherein the M in the general formula (I) is scandium Sc, yttrium Y, lutetium Lu, or lanthanum La.

4. The complex according to claim 1, wherein the X in the general formula (I) is N.

5. The complex according to claim 1, wherein the E$^1$ and E$^2$ in the general formula (I) each represent independently a diaryl phosphino group, a dialkyl phosphino group, or an alkylaryl phosphino group.

6. A complex represented by the following general formula (II):

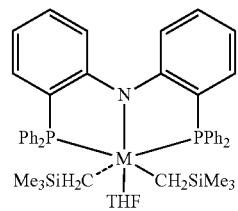

(II)

wherein in general formula (II), M represents scandium Sc, yttrium Y, lutetium Lu, or lanthanum La.

7. A complex represented by the following general formula (III):

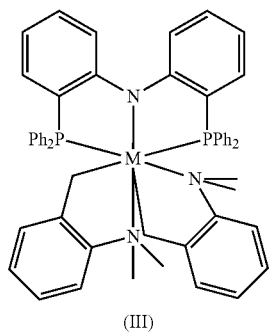

(III)

wherein in general formula (III), M represent scandium Sc, yttrium Y, lutetium Lu, or lanthanum La.

8. A polymerization catalyst composition, comprising the complex according to claim 1.

9. The polymerization catalyst composition according to claim 8, further comprising a catalyst activator.

10. The polymerization catalyst composition according to claim 9, wherein the catalyst activator is an ionic compound made of a non-coordination anion and a cation.

11. The polymerization catalyst composition according to claim 10, wherein the non-coordination anion is a quadrivalent boron anion.

12. The polymerization catalyst composition according to claim 8, which is used for polymerization of olefin.

13. The polymerization catalyst composition according to claim 12, wherein the olefin is at least one of isoprene, butadiene, or styrene.

14. A process for producing a polymer, comprising: polymerizing additional polymerizable monomers utilizing the polymerization catalyst composition according to claim 8.

15. The process according to claim 14, wherein the additional polymerizable monomer is olefin, and the polymer is an olefin polymer.

16. The process according to claim 15, wherein:
the additional polymerizable monomer is at least one of isoprene, butadiene, or styrene; and
the polymer is an isoprene polymer, a butadiene polymer, a styrene polymer, a butadiene-isoprene copolymer, a butadiene-styrene copolymer, an isoprene-styrene copolymer, or a butadiene-isoprene-styrene copolymer.

* * * * *